(12) United States Patent
Byrne et al.

(10) Patent No.: US 7,384,733 B1
(45) Date of Patent: Jun. 10, 2008

(54) INTERFACE PATCH CLAMPING

(75) Inventors: Nicholas Gerard Byrne, Suffolk (GB); David Geraint Owen, Kent (GB)

(73) Assignee: Xention Discovery Limited, London (GB)

(*) Notice: Subject to any disclaimer, the term of this patent is extended or adjusted under 35 U.S.C. 154(b) by 0 days.

(21) Appl. No.: 09/857,456

(22) PCT Filed: Dec. 6, 1999

(86) PCT No.: PCT/GB99/04073

§ 371 (c)(1),
(2), (4) Date: Sep. 24, 2001

(87) PCT Pub. No.: WO00/34776

PCT Pub. Date: Jun. 15, 2000

(30) Foreign Application Priority Data

| Dec. 5, 1998 | (GB) | ................................. | 9826742.0 |
| Mar. 17, 1999 | (GB) | ................................. | 9905998.2 |
| Mar. 17, 1999 | (GB) | ................................. | 9906053.5 |

(51) Int. Cl.
*C12Q 1/00* (2006.01)
*C12Q 1/02* (2006.01)
*C12M 1/34* (2006.01)
*C12M 3/00* (2006.01)

(52) U.S. Cl. ........................... 435/4; 435/29; 435/287.3; 435/288.3; 204/403.01; 205/777.5

(58) Field of Classification Search ................ 435/325, 435/173.1, 174.4, 4, 29, 287.3, 288.3; 424/93.7; 204/403.01; 206/777.5
See application file for complete search history.

(56) References Cited

U.S. PATENT DOCUMENTS

| 4,897,426 | A |   | 1/1990 | Llinas et al. |
| 5,225,374 | A |   | 7/1993 | Fare et al. |
| 5,234,566 | A |   | 8/1993 | Osman et al. |
| 5,643,796 | A |   | 7/1997 | Van den Engh et al. |
| 5,874,668 | A | * | 2/1999 | Xu et al. ........................ 73/105 |
| 5,981,268 | A |   | 11/1999 | Kovacs et al. |
| 6,063,260 | A |   | 5/2000 | Olesen et al. |
| 6,455,303 | B1 | * | 9/2002 | Orwar et al. ............. 435/287.1 |

FOREIGN PATENT DOCUMENTS

| DE | 197 12 309 A1 | 5/1998 |
| DE | 197 44 649 A1 | 4/1999 |
| DE | 198 41 337 C1 | 9/1999 |
| JP | 9211010 | 8/1997 |
| WO | WO89/01159 | 7/1988 |
| WO | WO96/36436 | 4/1996 |
| WO | WO 96/13721 | 5/1996 |
| WO | WO97/20203 | 11/1996 |
| WO | WO97/25616 | 1/1997 |
| WO | WO98/23948 | 11/1997 |
| WO | WO99/19729 | 10/1998 |
| WO | WO 98/50791 | 11/1998 |
| WO | WO 98/55870 | 12/1998 |
| WO | WO99/66329 | 6/1999 |
| WO | WO00/34776 A1 | 12/1999 |
| WO | WO01/71349 | 3/2001 |
| WO | WO01/94939 | 6/2001 |

OTHER PUBLICATIONS

Anderson, M.T. et al., "Simultaneous fluorescence-activated cell sorter analysis of two distinct transcriptional elements within a single cell using engineered green fluoresent proteins," Proc. Natl. Acad. Sci USA, vol. 93, pp. 8508-8511 (1996).
Brew, Helen et al., "Electrogenic glutamate uptake is a major current carrier in the membrane of axolotl retinal glial cells," Nature, vol. 327, pp. 707-709 (1987).
Fu, Anne Y. et al., "A microfabricated fluorescence-activated cell sorter," Nature Biotechnology, vol. 17, pp. 1109-1111 (1999).
O.P. Hamill et al., "Improved Patch-Clamp Techniques for High-Resolution Current Recording from Cells and Cell-Free Membrane Patches," Plugers Archiv., European Journal of Physiology, pp. 85-100 (1981).
"Lecture 5: Electrophysiological Techniques," BIOL 445—1997 Notes on the www.
Margolskee, Robert F., et al., "Panning Transfected Cells for Electrophysiological Studies," Research Report—BioTechniques, vol. 15, No. 5, pp. 906-911 (1993).
Sheng, Morgan, "PDZs and Receptor/Channel Clustering: Rounding Up the Latest Suspects," Neuron, vol. 17, pp. 575-578 (1996).
Stephens, Gary J. et al., "On the mechanism of 4-aminopyridine action on the cloned mouse brain potassium channel mKv1.1," Journal of Physiology, pp. 187-196 (1984).
Winegar, Bruce, "Obtaining Gigaohm Seals" Eleusis Patch Clamp Resources (1999).
Molleman, "Patch Clamping, An Introduction to Patch Clamp Electrophysiology," John Wiley & Sons, Ltd. (2003) pp. 103-104.
Higashi et al., "Preparation and some properties of giant liposomes and proteoliposomes," J Biochem (1987) 101(2):433-440; http://www.citeulike.org/user/davidng/article/100090, printed Jul. 14, 2006 (3 pages).
Lynch, "PHYS2170: Electrophysiological techniques II: Patch-clamping," http://www.biophysics.org/btol/img/Ypev-Part1.pdf.

(Continued)

*Primary Examiner*—Blaine Lankford
*Assistant Examiner*—Thane Underdahl
(74) *Attorney, Agent, or Firm*—Morgan Lewis & Bockius LLP

(57) ABSTRACT

The invention provides a novel development of the conventional patch clamp technique for measurement of whole cell electrical activity. The invention provides for one or more cell or cells to be suspended in a liquid medium at a liquid/air interface (by virtue of the effect of surface tension at the interface) whereby the cell or cells are accessible at the interface to a microstructure electrode (such as a pipette tip) to which a cell can attach to form an electrical seal, for the purpose of whole cell voltage clamp recording. According to the invention the electrode can be caused to form a high resistance electrical seal with a cell suspended in the liquid at the liquid/air interface without the need to press the cell against a solid support surface. The invention also provides apparatus for carrying out the interface patch clamp technique and control logic for operating a computer to carry out the interface patch clamp technique.

15 Claims, 33 Drawing Sheets

OTHER PUBLICATIONS

Lehmann-Horn et al., "Nanotechnology for neuronal ion channels," http://jnnp.bmjjournals.com/cgi/content/full/74/11/1466, printed Jul. 14, 2006 (18 pages).

Week Six: Patch Clamping, http://www2.uic.edu/~bnardu1/week_six.htm, printed Jul. 14, 2006 (2 pages).

* cited by examiner

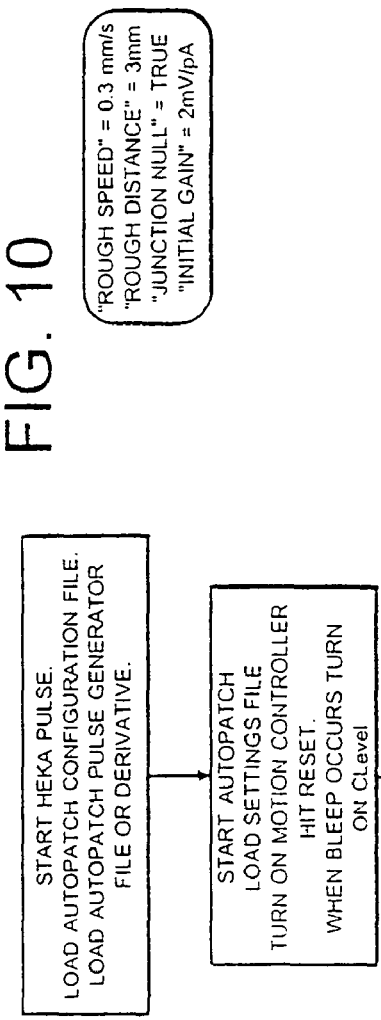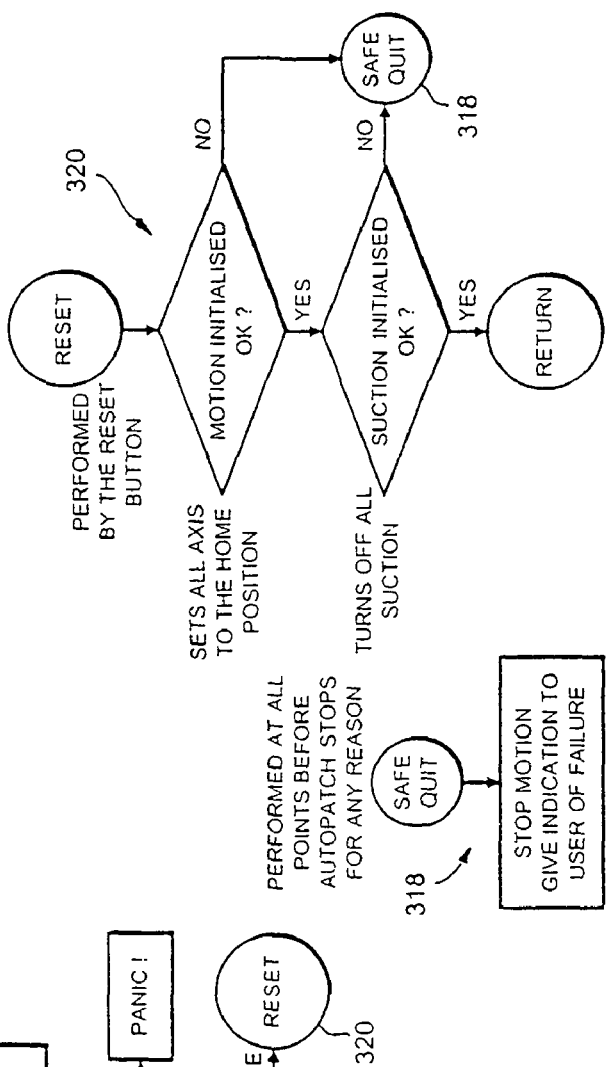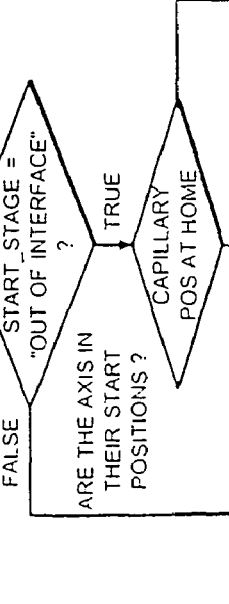
FIG. 10
FIG. 10a
FIG. 10b

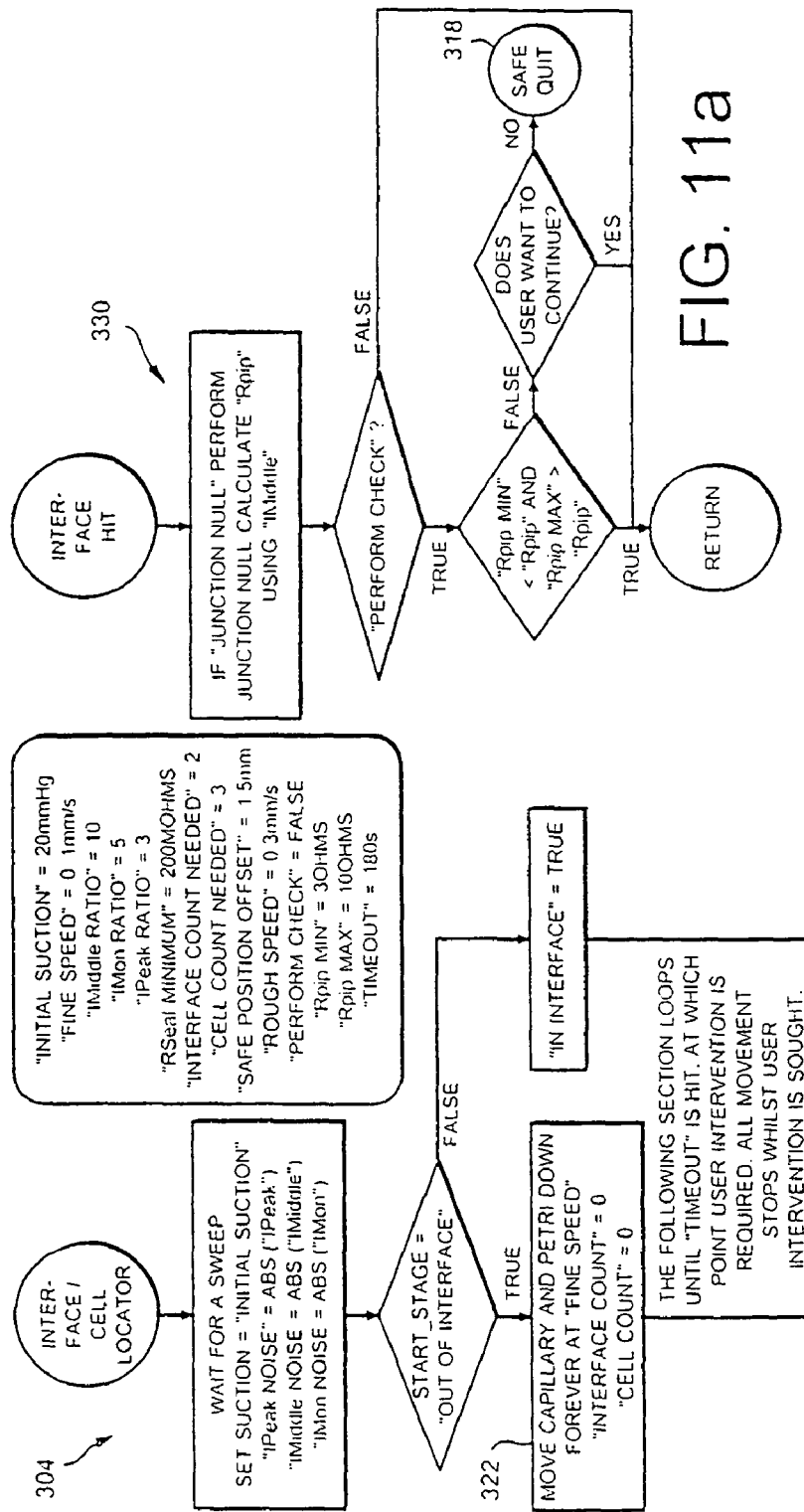

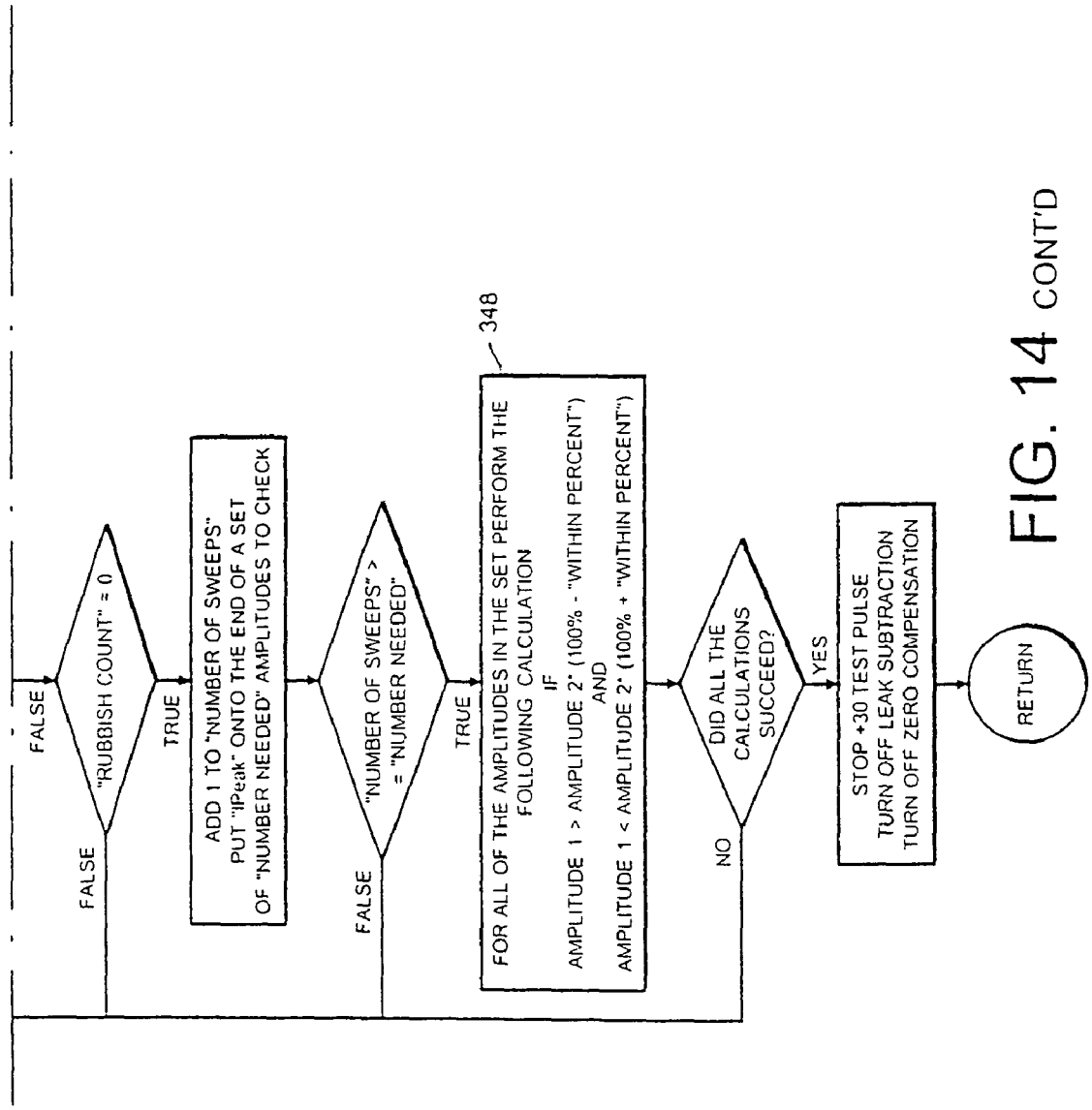

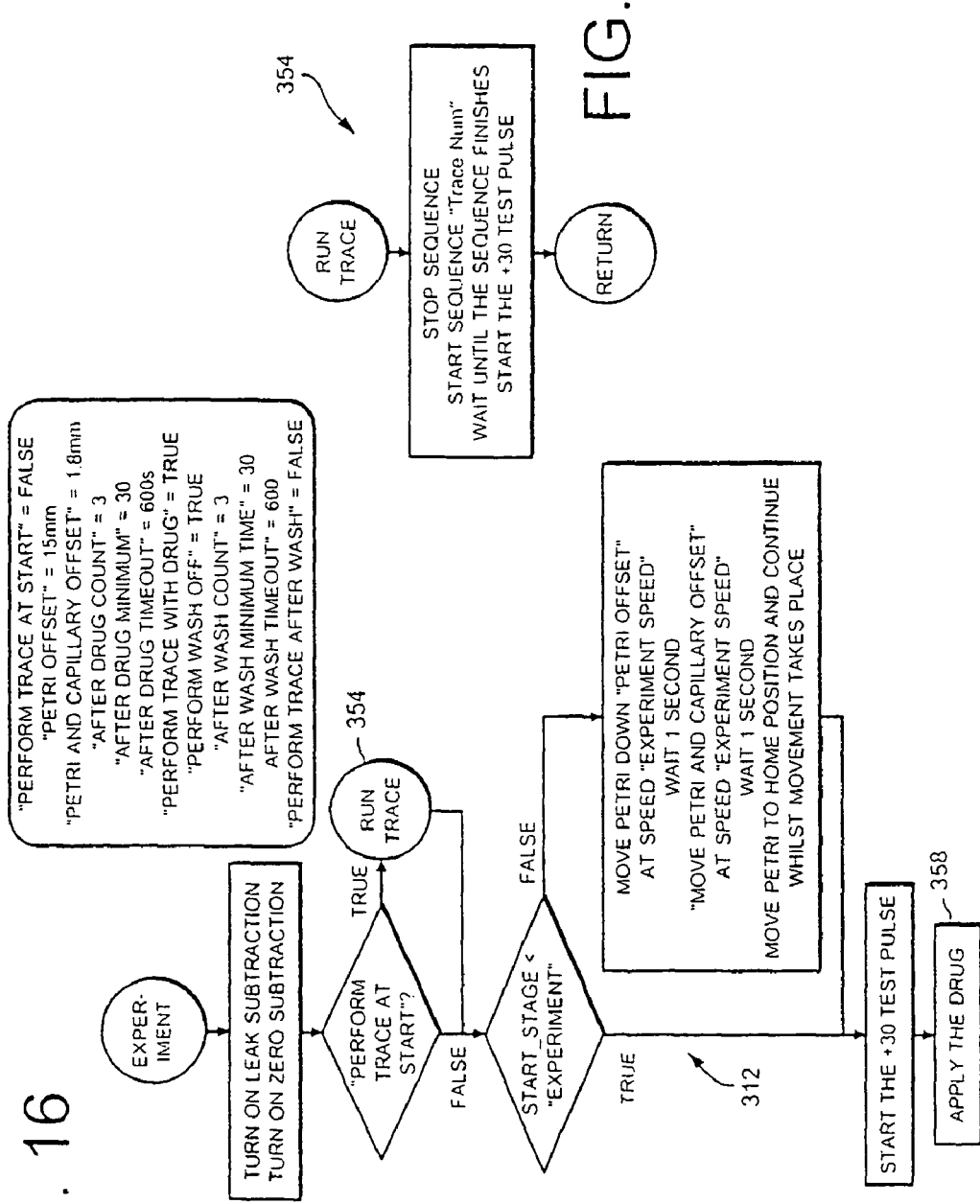

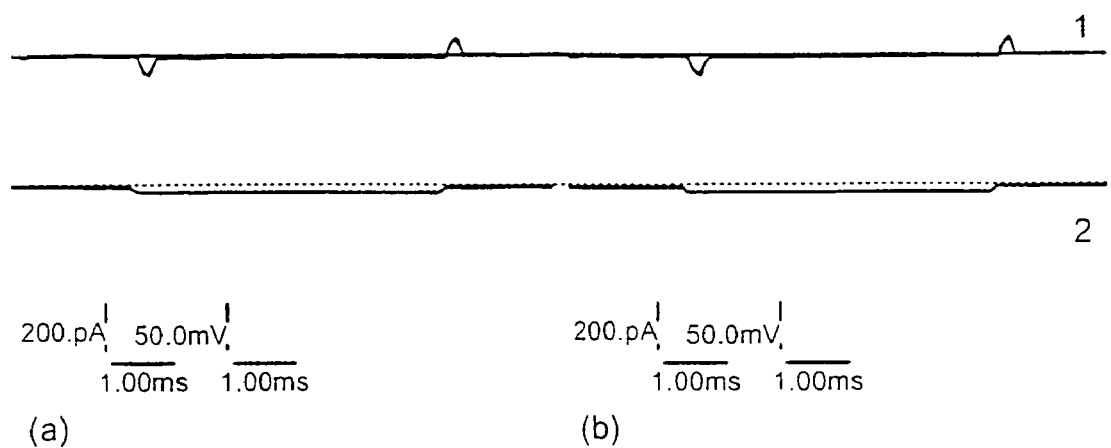
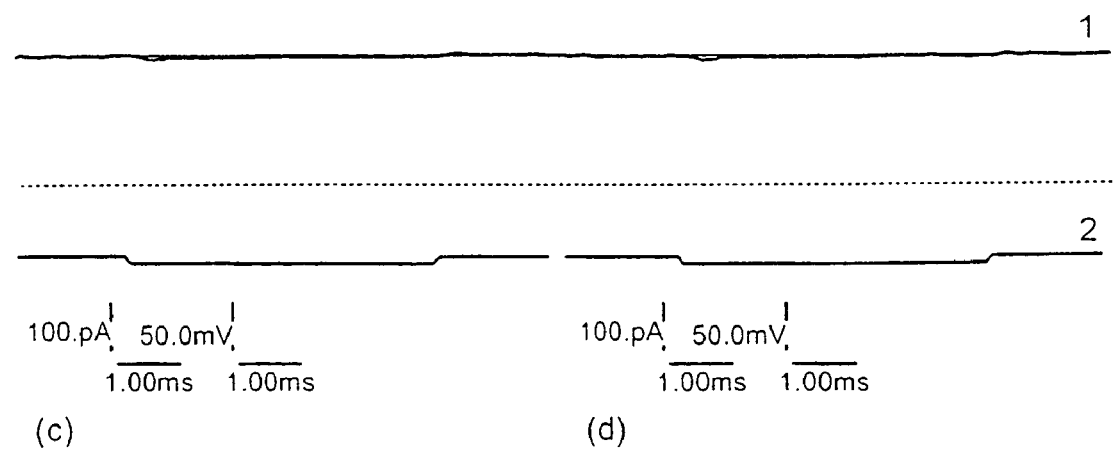
FIG. 18

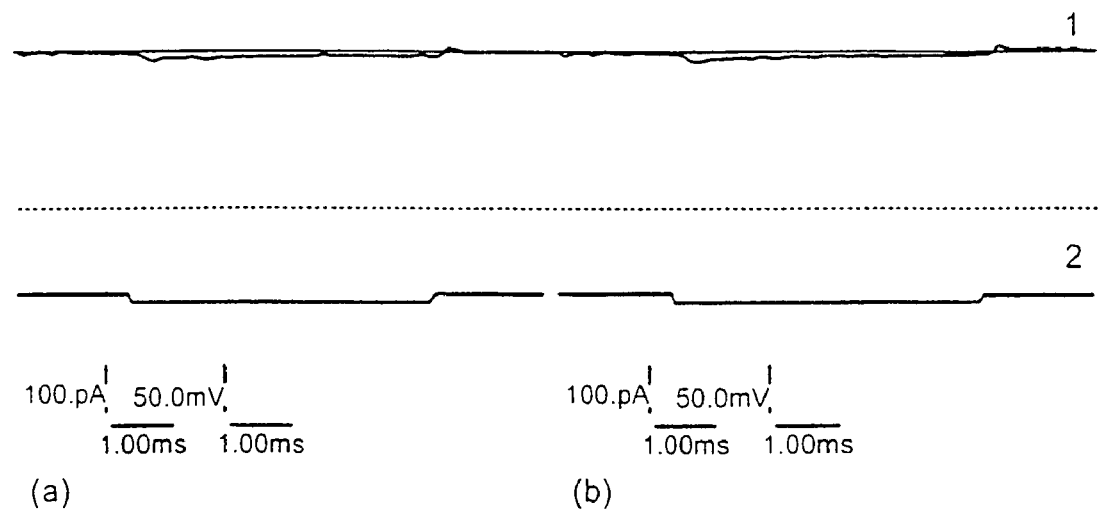
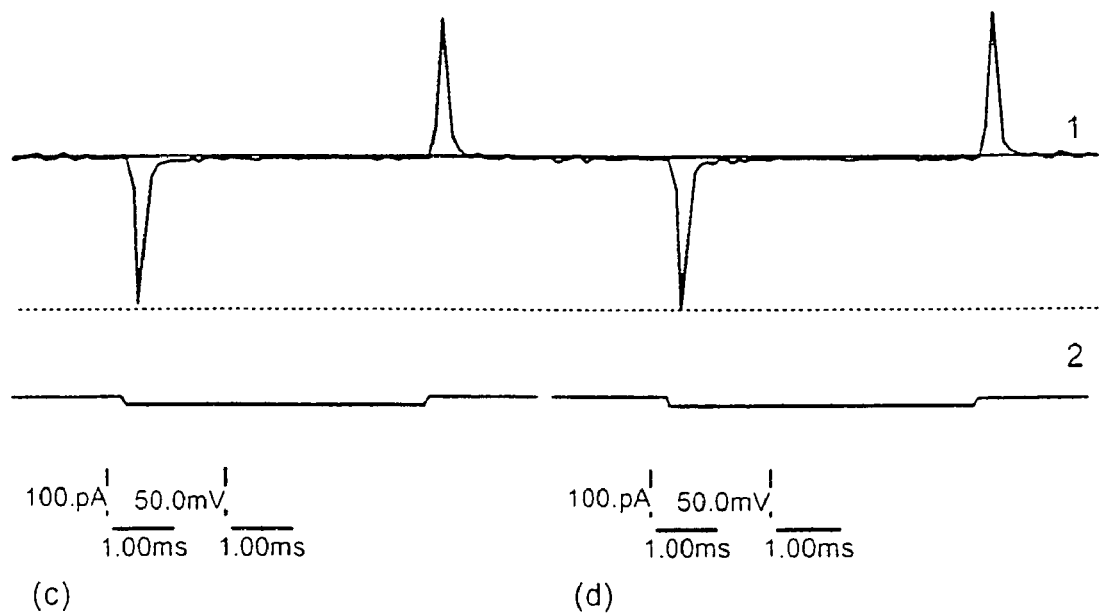
FIG. 19

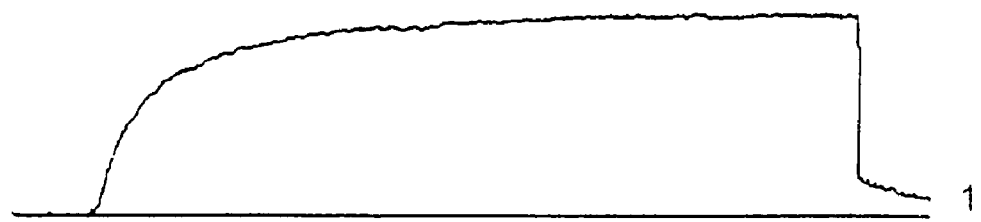
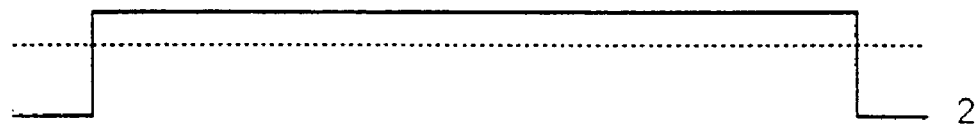
500.pA | 50.0mV |
20.0ms   20.0ms
(a)
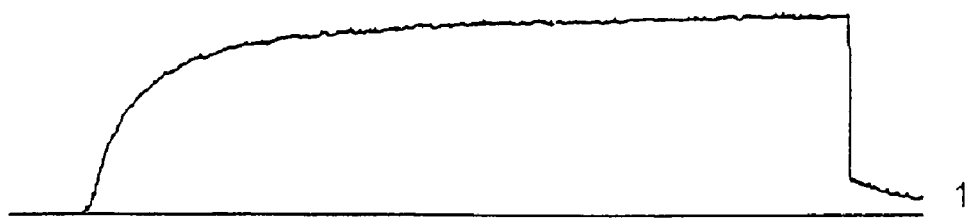
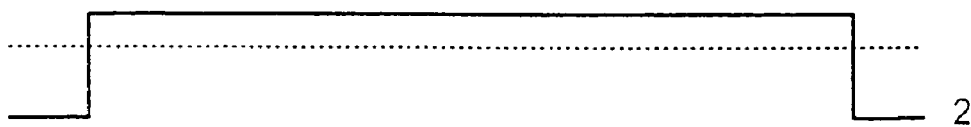
500.pA | 50.0mV |
20.0ms   20.0ms
(b)
FIG. 20

(a)
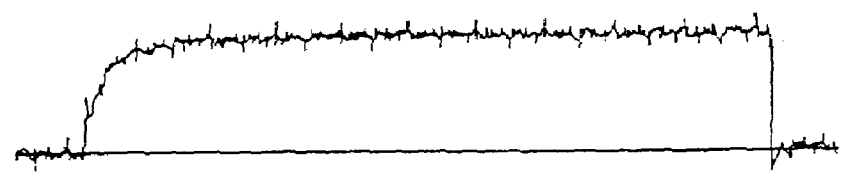
(b)
(c)
FIG. 21

INTERFACE PATCH CLAMPING

The present invention provides a novel development of the conventional patch clamp technique. This novel technique is referred to as the interface patch clamp method.

Voltage gated ion channels are potential targets for a considerable range of novel treatments in a variety of disease states. The development of the patch clamp technique has provided a powerful method for the study of ion channel function and pharmacology in whole cells. However, while the patch clamp technique provides a definitive method for the investigation and screening of drugs with potential activity on voltage gated ion channels, the technique is currently highly dependent on the skill of the operator and tends to be very slow for drug screening. The present invention provides a method for increasing the rate at which compounds may be screened for ion channel blocking/agonist activity using the patch clamp technique. The method can retain the essential features of the conventional patch clamp recording system while facilitating automation of the major time-consuming components of the technique.

BACKGROUND

Conventional Patch Clamp

The success of the patch clamp technique is derived from the ability to form "tight" (i.e. high resistance: Giga Ohm) electrical seals between an area of the cell membrane (the Patch) and the tip of a pipette. The patch clamp pipette is usually made from glass. The formation of the G-seal is dependent on the profile of the top of the pipette, and is enhanced by the application of suction to the interior of the pipette. The requirements for the formation of the G-seals are well established and the process is usually monitored electrically by display of the current pulse recorded in response to a small voltage step applied throughout seal formation. After formation of a G-seal, the area of membrane under the pipette may be disrupted to obtain whole cell voltage clamp recording mode.

The sequence of events leading to successful G-seal formation and whole cell recording mode using pre-formed patch pipettes is as follows:
1. Selection of a suitable cell.
2. The patch pipette is positioned approximately 50 microns above the cell.
3. The pipette is lowered until the cell surface is deformed by the pipette tip.
4. Negative pressure is applied to the interior of the pipette until a G-seal is formed between the pipette tip and the cell membrane.
5. Whole cell recording mode is established by the application of further negative pressure which disrupts the cell membrane in the area under the pipette tip.

Steps two and three are slow and require considerable manual dexterity and a high level of operator skill. Visualization of the cells and the patch pipette requires the use of a high quality microscope and, in order to position the pipette, a high quality three axis micromanipulator with sub-micron resolution in each axis is required.

SUMMARY OF THE INVENTION

In its broadest terms the invention provides for one or more cell or cells to be suspended in a liquid medium at a liquid/air interface (by virtue of the effect of surface tension at the interface) whereby the cell or cells are accessible at the interface to a microstructure electrode (such as a pipette tip) to which a cell can attach to form an electrical seal, for the purpose of whole cell voltage clamp recording. According to the invention the electrode can be caused to form a high resistance electrical seal with a cell suspended in the liquid at the liquid/air interface without the need to press the cell against a solid support surface.

Any body of liquid or column of liquid, which gives rise to a situation in which a cell or cells are located in the liquid at a liquid/air interface, can be used in the invention. For examples cells may be suspended in a column of liquid held by surface tension in a capillary tube. Alternatively cells may be suspended in a droplet of liquid, which droplet may itself be suspended from or supported by a support.

It will readily be appreciate that the interface patch clamp technique can be operated in a "single cell mode", or could be multiplexed to operate on a matrix of cells with multiple electrodes.

According to one aspect of the invention, interface patching can utilize a patch pipette of conventional type. Cells are supported on a liquid/air interface at one end of a capillary tube (e.g. made of glass, polyethylene or other suitable material). The axis of the patch pipette is in line with the axis of the tube so that the pipette tip can be manipulated into the opening of the tube where the cells are supported at the air/liquid interface. The capillary tube or the patch pipette can be mounted onto a single axis manipulator. Only one manipulator is required and this may be used to move either the patch pipette or the capillary tube. Whole cell recording mode is established as follows:

6. A layer of cells is established at the interface between the extracellular physiological solution (the liquid in which the cells are suspended) and air by dipping the capillary tube into a suspension of cells. The density of cells in the suspension must be sufficient to provide a sufficient number of cells to form a layer of cells at the interface.
7. Electrical contact with the extracellular solution is established via a non-polarizable electrode (e.g. an Ag/AgCl wire) and the tube is mounted either to a fixed clamp or single axis manipulator.
8. A patch pipette is provided which can be filled with electrolyte solution.
9. The patch pipette is mounted concentrically with the capillary tube either via a single axis manipulator or fixed clamp (if the capillary tube is to be moved). The pipette filling solution is connected via the non-polarizable electrode to the headstage of a conventional patch clamp amplifier. The pipette holder allows suction to be applied to the pipette interior.
10. Cell attached patch mode of recording is established by bringing the pipette tip in contact with the interface by moving the pipette and the capillary tube respectively together along the single mounting axis (e.g. either by moving the pipette towards the tube and interface or vice versa). On entry into the interface the movement of the pipette and capillary tube together is stopped and the pipette current is offset to zero on the patch clamp amplifier. The resistance of the pipette increases when the pipette contacts one of the cells at the air/liquid interface. Suction is then applied to the interior of the pipette and the pipette and capillary tube are moved closer together until the pipette tip is located inside the capillary tube.

Initial seal formation between the pipette tip and the cell may also be assisted by the application of gentle suction during entry of the pipette into the interface.

A G-seal is formed between the patch pipette tip and the cell membrane by the application of further suction to the interior of the pipette and monitoring the pipette resistance.

11. Following the formation of cell attached patch mode, the suction is released, pipette current is offset to zero and a holding voltage applied to the pipette (e.g. −60 mV).

12. A whole cell recording is obtained by the application of further suction to the pipette interior until the whole cell recording mode is established in conventional manner.

According to this invention it is preferred that the capillary tube should be mounted in an upright orientation (i.e. essentially vertically) with the air/liquid interface at the downward end of the tube.

This has the advantage that suspended cells will tend to "sediment" naturally to the downward end of the tube and be collected there in a layer. The layer will preferably be several cells deep and loosely packed. Thus according to the invention the pipette tip may be moved upwardly relative to the air/liquid interface at the tube end (either by moving the pipette or the tube along the single axis) so as to come into contact with a cell in the layer at the interface. The relative density or concentration of cells at the interface compared to the density in the bulk of the liquid in the tube ensures a high probability that a cell can be collected on the tip without the need for visualization of the operation and without the need for multidirectional manipulation of the tip/cell positional relationship. Surprisingly it has been found that G-seal formation between the cell and the pipette can occur without pressing the cell against a solid substrate.

Where the arrangement is intended to operate with the pipette in an upright orientation (i.e. essentially vertically) with the tip uppermost and pointing upwardly, the pipette should be constructed so as to prevent the filling electrolyte solution flowing out and being lost. This may be achieved for example by use of a custom-made mounting assembly and/or by shaping the pipette body to prevent loss of filling solution (e.g by bending the pipette shaft into a U- or J-shape).

The invention also provides methods and apparatus employing control logic to allow automation of a patch clamp system employing the Interface Patch Clamp technique described herein. The logic described will control one or more electromechanical micromanipulators/translators holding one or more patch clamp pipettes and/or capillary tubes in order to patch clamp cells and apply drugs/compounds in order to screen for activity on membrane ion channels. A major advantage of the logic described is that automation is achieved in this system by the use of feedback from signals from the patch clamp amplifier and no image recognition software is required.

The invention is illustrated by way of example in the accompanying figures in which:

FIGS. 10 to 16 are flowcharts of a third embodiment of the control logic used in the invention, wherein FIG. 10 is a flow diagram of control logic embodying a further aspect of the invention;

FIG. 10a is a flow diagram expanding the reset routine of FIG. 10;

FIG. 10b is a flow diagram expanding the safe quit routine of FIG. 10;

FIG. 11 is a flow diagram expanding the interface or cell locator routine of FIG. 10;

FIG. 11a is a flow diagram expanding the interface hit routine of FIG. 11;

FIG. 12 is a flow diagram expanding the Giga seal test routine of FIG. 10;

FIG. 13 is a flow diagram expanding the whole cell detection routine of FIG. 10;

FIG. 14 is a flow diagram expanding the qualification routine of FIG. 10;

FIG. 15 is a flow diagram expanding the quality monitor routine of FIG. 14;

FIG. 16 is a flow diagram expanding the experiment routine of FIG. 10;

FIG. 16a is a flow diagram expanding the run trace routine of FIG. 16;

FIG. 16b is a flow diagram expanding the stabilize routine of FIG. 16;

FIGS. 17 to 20 show recordings of current (1) and voltage (2) obtained from an automated patch clamp system (Auto-Patch) under software control using the Interface Patch Clamp technique. (Recording from an MK1 cell);

FIG. 21 shows the effect of the potassium channel blocking drug tetraethylammonium (TEA) on the potassium current recorded from MK1 cell in whole cell recording mode obtained using the Interface Patch Clamp technique;

Figure 1A:
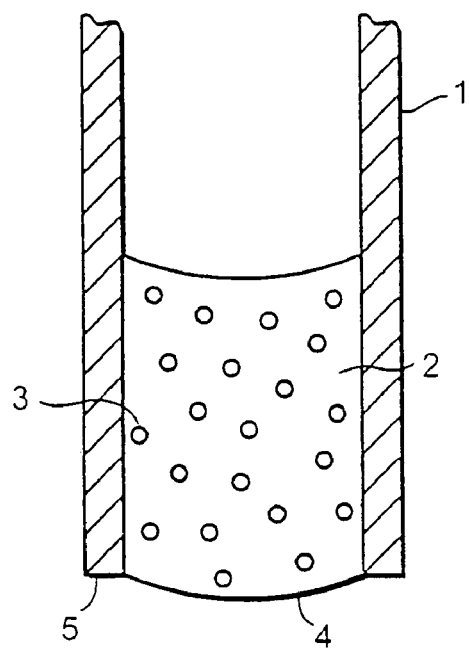
FIG. 1a shows a capillary tube containing a suspension of cells.

Referring to FIG. 1a; a capillary tube (1) of appropriate size can pickup and hold a liquid sample (2) containing cells (3) in suspension. The sample can be picked up simply by dipping the tube end into a suitable bulk liquid reservoir. The liquid in the tube forms an air/liquid interface (4) at the tube end (5). The cells are initially distributed throughout the liquid relatively evenly.

Figure 1B:
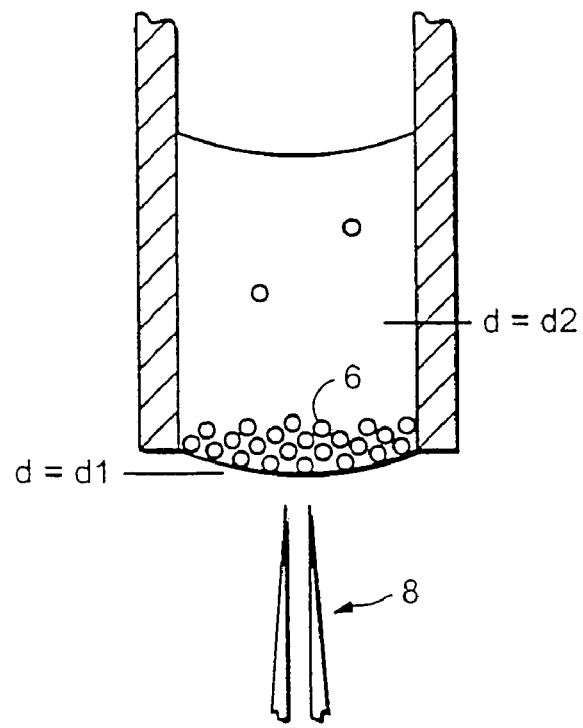
FIG. 1b shows the cells having formed a layer at the air/liquid interface at one end of the capillary tube.

Referring to FIG. 1b; with the tube in an upright essentially vertical orientation, the cells tend to sediment and to pack loosely together at the lower end of the tube by the tube end to form a layer (6) several cells deep. It will be appreciated by those skilled in the art that the density and depth of the cell layer can be determined by such factors as the cell concentration in the original suspension, the sedimentation time, the relative density of the cells and the liquid etc. It will also be appreciated that means could be devised to encourage or assist cells to migrate from the liquid towards the air/liquid interface rather than or as well as relying on gravitational sedimentation alone. The Figure also shows the top of a patch pipette 8 pointing upwardly towards the interface.

Figure 2:
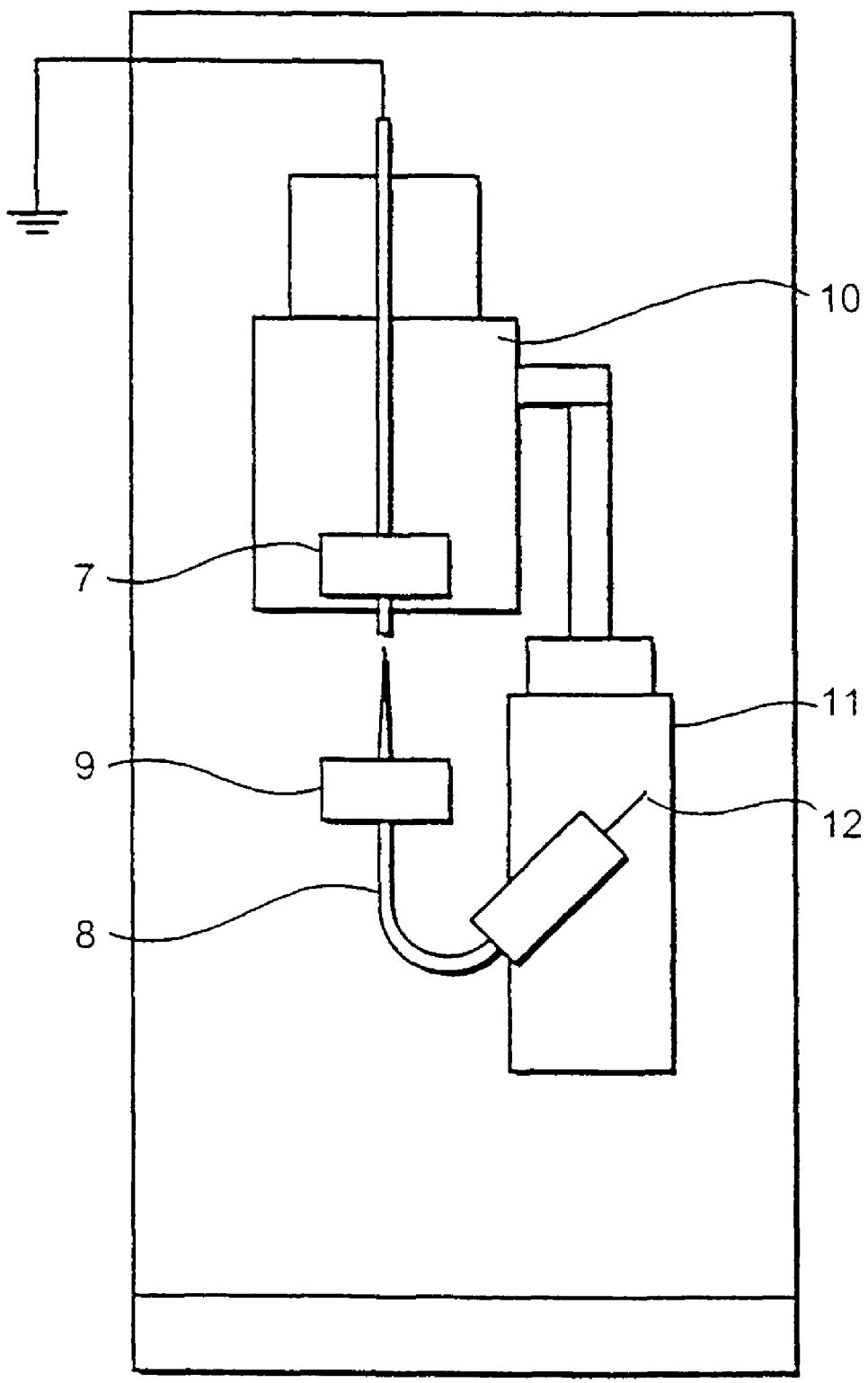
FIG. 2 shows a general arrangement of the interface patch clamp recording equipment with moveable capillary tube.

Referring to FIG. 2; an arrangement is shown in which a single axis manipulator is used to move a capillary tube 1 held in a clamp (7) relative to a fixed patch pipette (8) held in a clamp (9). It will be apparent to those skilled in the art that this could be reversed so that the pipette is moved and the tube is fixed. The Figure shows the tube clamped in a linear bearing sliding block (10) attached to a motorized single axis manipulator (11). The manipulator should be controlled preferably by computer in order to allow the motion of the manipulator to be varied by feedback from the patch clamp amplifier. The patch pipette is provided with a connection (12) to a conventional headstage. The system is also provided with a source of variable suction under the control of the patch clamp amplifier/computer.

Figure 2A:
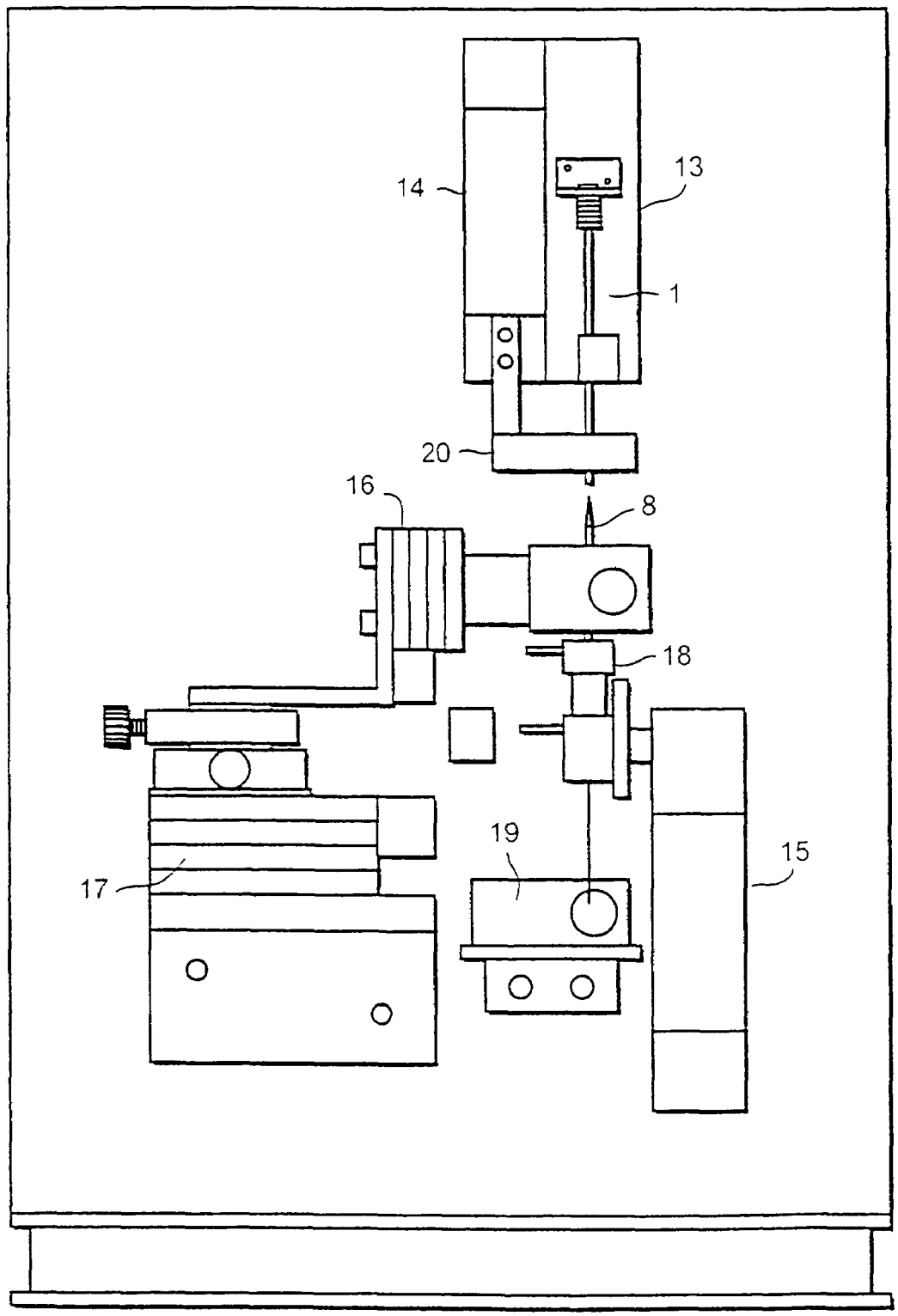
FIG. 2a shows an Apparatus for Interface Patch Clamping with drug/compound application.

In FIG. 2a an arrangement is shown in which additional electromechanical micromanipulators have been added. The microencapsulator labelled (13) is for moving the glass capillary under automated or manual control. A second micromanipulator (14) moves the dish for drug application up and down the glass capillary. A third micromanipulator (15) moves a modified pipette holder to provide electrical contact with the pipette and a means of applying suction to the interior of the pipette. Rotational bases (16 and 17) allow the pipette holder to be moved in and out of the recording area and rotation of the pipette through 180 degrees for filing with pipette solution.

The Figure also shows additional features, namely; a pipette holder (18); a patch clamp headstage (19); and a dish holder (20).

A version of the apparatus is envisaged in which path pipettes will be loaded and filled automatically under software control. It is envisaged also that the loading of capillary glass into the apparatus and the filling with cell suspension will also be automated.

Figure 3:
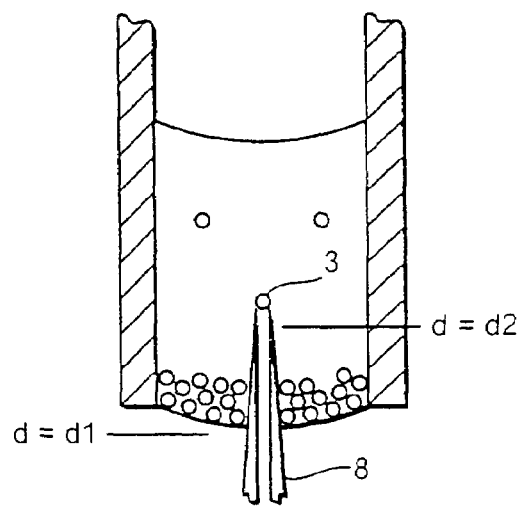
FIG. 3 shows the cell attached to the patch pipette ready for recording mode.

Referring to FIG. 3; a G-sealed cell 3 is shown held on the tip of the patch pipette 8 and positioned within the entrapped liquid volume in the tube.

Cell attached patch and whole cell (voltage clamp) recording may then be carried out.

The invention described herein has a number of significant features:

Visualization of the pipette and the cell is not required.
Novel recording configuration that would not be considered as obvious.
Surprisingly G-seal formation occurs without pressing the cell against a hard substrate.
Cells form a layer at the solution-air interface.
G-seal formation may be achieved using electronic feedback alone.
There is no requirement for optical recognition/feedback.
The system can be automated.
Multiple recording capillaries and pipettes may be employed in order to allow recordings to be made simultaneously from many cells.
Exemplary methods of operation of the apparatus of the embodiment under software control to achieve various of these advantages are described below.

In order to use the invention for screening compound (e.g. for ion channel blocking/agonist activity) the compound of interest needs to be applied to the cell attached to the patch pipette. It will readily be appreciated that this could be achieved in different ways, for example by adding the compound to the extracellular liquid in the capillary tube either before or after G-seal formation. One additional advantage of the invention is that the liquid in the tube could be arranged in layers (e.g. containing different compounds or different concentrations of compounds) and the single axis manipulator could then be used to physically move and position a cell on a pipette tip into a chosen layer (e.g. by moving the G-sealed cell on the tip further up the tube away from the air/liquid interface at one tube end).

A further example of how the effects of compounds may be studied is illustrated in FIGS. 4 to 7.

Figure 4:
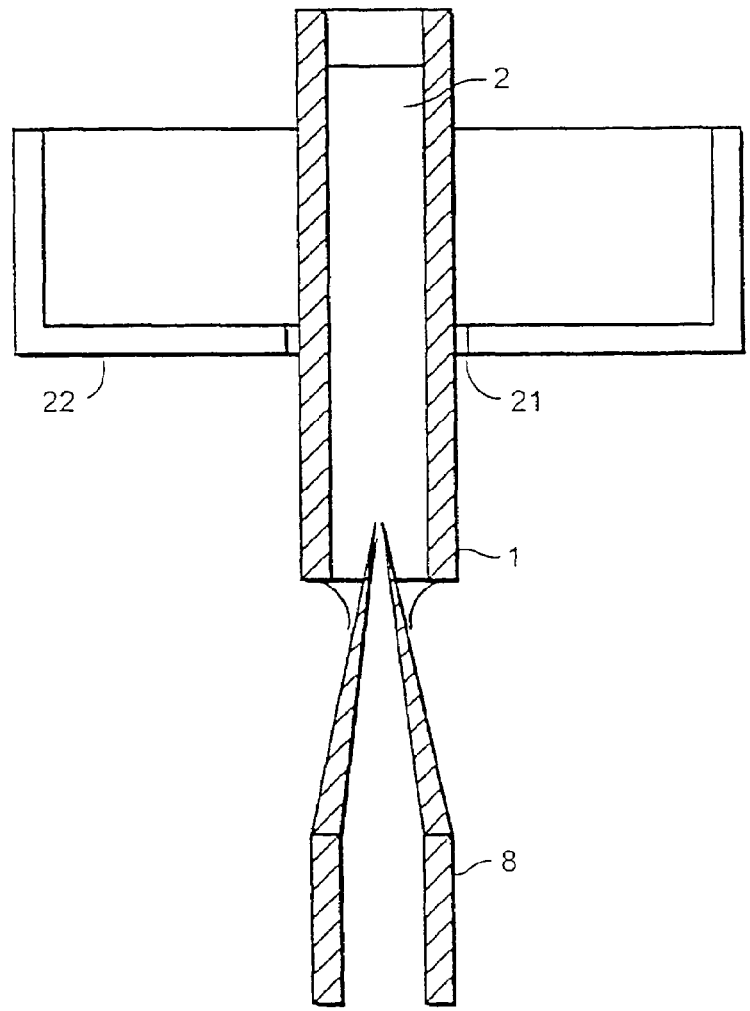
FIG. 4 shows drug/compound addition during interface patch clamp recording: start position.

FIG. 4 shows a capillary (1) containing the cell suspension (2) and patch pipette (8) in the recording position for whole cell recording from a cell at the pipette tip. In addition, the capillary tube has been inserted through a hole (21) made in a dish (22) (e.g. 35 mm plastic culture dish or similar). The dish is made of a material with hydrophobic properties and the hole allows the dish to be raised and lowered along the axis of the capillary by means of a micromanipulator (14).

Figure 5:
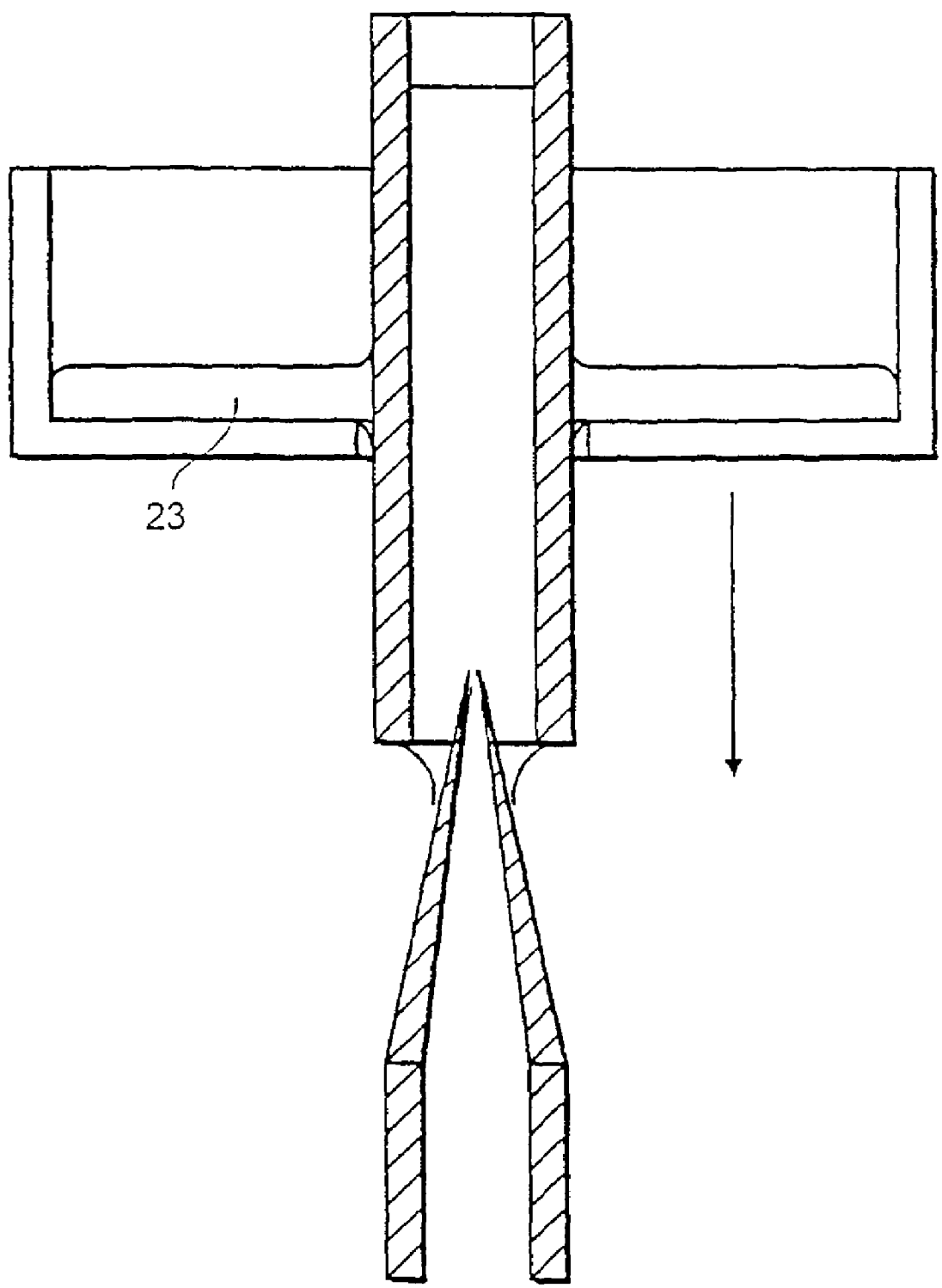
FIG. 5 shows drug/compound addition during interface patch clamp recording: extracellular solution added to dish and dish moved down.

FIG. 5 shows the dish after it has been filled with extracellular physiological solution (23), which may contain the drug to be studied, or the drug may be added at a later stage. Surprisingly, if the fluid level in the dish is low, leakage through the hole does not occur because the tendency to leak is counterbalanced by:

1. The surface tension of the water
2. The attraction of the water/solution to the glass capillary.

After adding the solution to the dish, it is lowered in the direction of the arrow.

Figure 6:
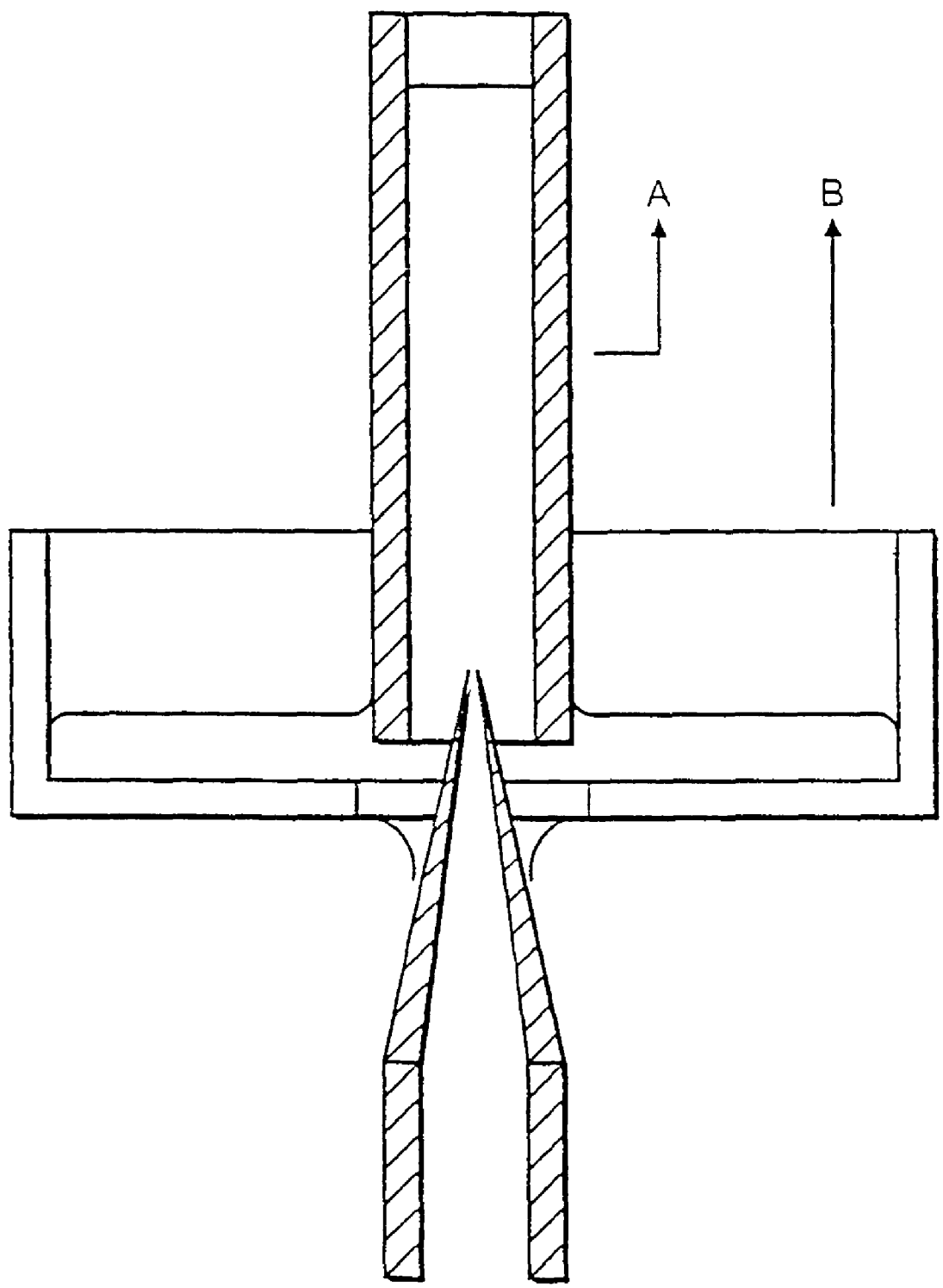
FIG. 6 shows drug/compound addition during interface patch clamp recording: solution in dish brought into contact with interface region.

FIG. 6 shows the solution in the dish in contact with the end of the glass capillary and the patch pipette. The dish and the capillary are now raised simultaneously (arrows A and B) in order to position the pipette tip/cell within the layer of liquid in the dish. If drug is present in the dish at this point and the capillary and dish were moved upwards rapidly, this would constitute a rapid application system particularly useful for the study of agonist responses that desensitize.

Figure 7:
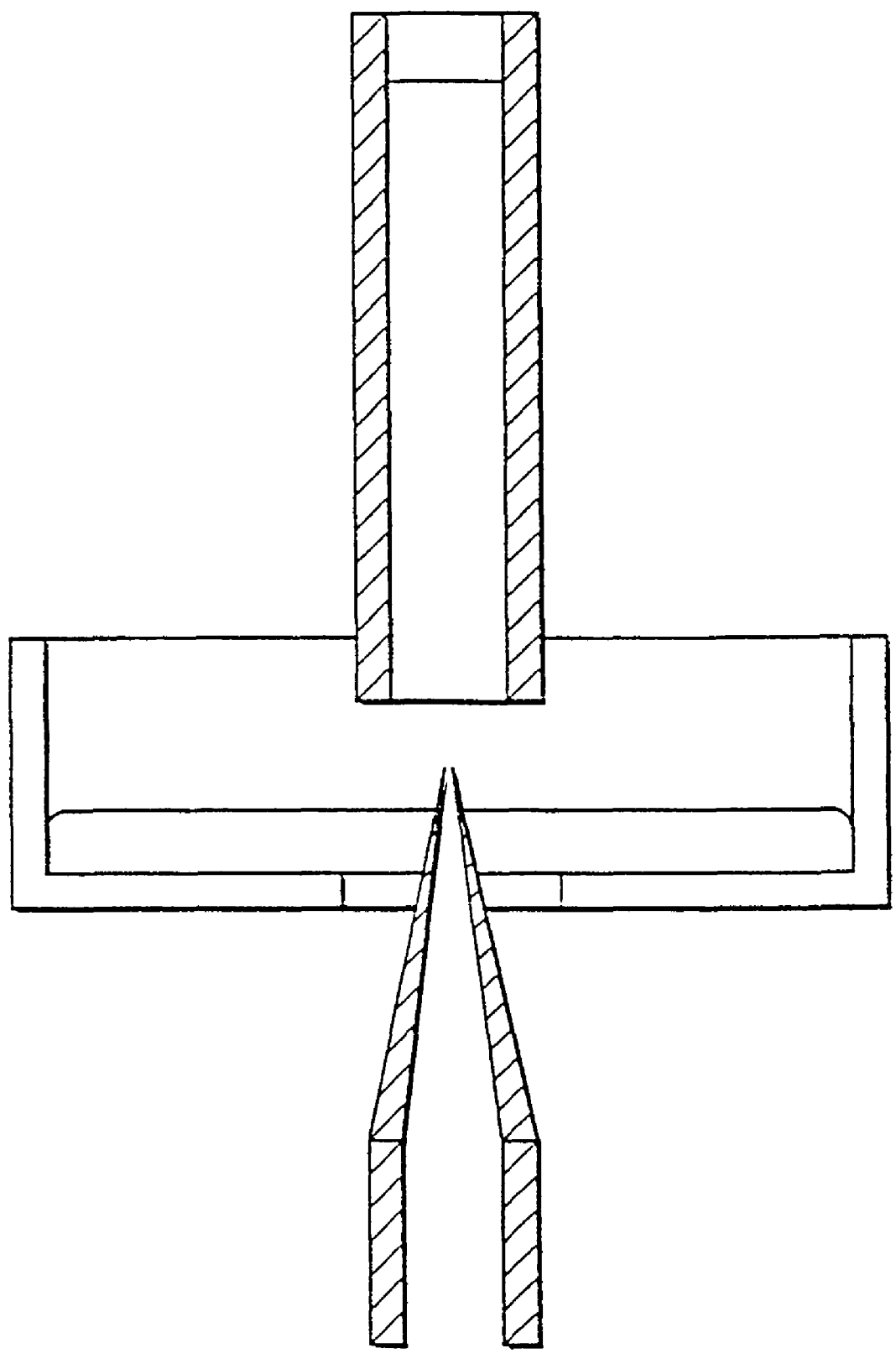
FIG. 7 shows drug/compound addition during interface patch clamp recording: capillary raised above surface of solution in dish.

FIG. 7 shows the effect of raising the capillary so that it is not in contact with the liquid in the dish. The pipette tip/cell remains immersed in the external solution layer in the dish. The solution may be exchanged readily by perfusion of the dish and this allows multiple drug additions and dose response curves to be obtained while recording from the one cell.

CONTROL LOGIC FOR AN AUTOMATED PATCH CLAMP SYSTEM

Introduction

The following describes three embodiments of the control logic required to allow automation of a patch clamp system employing the Interface Patch Clamp technique described herein. In each case, the logic described will control one more more electromechanical micromanipulators/translators in order to patch clamp cells and apply drugs/compounds in order to screen for activity on membrane ion channels. A major advantage of the logic described is that automation is achieved in this system by the use of feedback from signals from the patch clamp amplifier and no image recognition software is required.

Methods

Inputs to the program in all the embodiments are required from the patch clamp amplifier as follows:
Imon=current monitor output
Vhold=holding potential
Inputs to the program derived from patch clamp amplifier output signals are required as follows:
Inoise=base line current noise recorded from Imon
Rpip=pipette resistance
Rtot=Total resistance
Rs derived from Imon signal during voltage step It is envisaged that these signals and evaluated values will be obtained from existing software (such as Heka software) via a suitable software interface. These signals and evaluated values are further defined in the list of variables and parameters below.

Inputs from manipulators/translators are required as follows, or from the following devices.
Patch module micromanipulator encoder
Capillary clamp/loader encoder and empty signal
Pipette automated clamp/loader encoder and empty signal
Two axis translator encoders for cell dipper
Drug application micromanipulator encoder
Pipette holder micromanipulator encoder Control outputs from computer are required for the following devices.
Patch module manipulator
Pipette automated holder
Capillary loader/clamp
Pipette loader/clamp
Two axis translator for cell loading system
Pipette clamp
Suction device
Drug application manipulator
Drug perfusion solenoid valve system The software uses signals derived from the patch clamp amplifier in order to control a number of peripheral devices which carry out patch clamping using the Interface Patch Clamp technique. The devices controlled by the logic comprise a number of micromanipulators, a suction device for the patch pipette and a valve system for perfusion of a recording chamber, such as the dish described above.

A number of parameters are given pre-set values which can be changed by the operator to suit different experimental conditions.

Summary of the Control Logic for the Automated Interface Patch Clamp—First Embodiment

Initial Seal Formation

The sequence of movements required for formation of a G-seal is unique for interface patch clamping and involves the control of at least one single axis manipulator (e.g. the patch module motor, although either the pipette or the capillary may be moved to achieve the necessary relative movement between them) with feedback from the patch clamp amplifier. In a first embodiment of the control logic, the pipette is initially spaced from the capillary, as illustrated in FIG. 1b for example, and is moved towards the liquid/air interface at the capillary end until a change in the current monitor signal is recorded when the patch pipette enters the liquid/air interface and this signal is used as the trigger to stop the micromanipulator. The pipette resistance may be derived from the output of the patch clamp amplifier and initial seal formation is monitored by recording the change in pipette resistance. If the resistance of the pipette does not increase beyond a pre-set value, the control logic infers that no G-seal has been formed and activates the patch module motor to move the liquid/air interface and the pipette apart until the resistance increases, which may occur when the pipette tip is withdrawn from the liquid or when a narrow neck of liquid is drawn out by surface tension between the pipette tip and the capillary end. When a resistance increase to a pre-set value is recorded suction is applied to the interior of the patch pipette and the patch pipette and the liquid/air interface are moved towards each other to a pre-set point, in a further attempt to form a G-seal with a cell.

Whole Cell Recording Mode

After formation of the cell attached patch clamp recording mode, whole cell mode is obtained by the application of suction to the interior of the patch pipette while simultaneously monitoring the current (Imon) for capacitative transients. In the logic described, the formation of whole cell recording mode is detected by a threshold crossing method but it will be apparent to those skilled in the art that other methods may also be employed e.g. online FFT (Fast Fourier Transform), Template Matching etc. The control logic checks for incorrect detection of whole cell mode before activating the experimental protocol.

Cell Quality Test

This routine monitors the quality of voltage clamp by comparing the series recorded resistance with a value related to pipette resistance. It will be appreciated that this method may be further enhanced by relating the acceptable series resistance to the amplitude of current evoked by a voltage step. In addition, an additional loop may be added to include the possibility of recording with a maintained level of suction applied to the pipette in cells that exhibit continuously increasing values of series resistance. The quality of the cell is also monitored by the holding current which should not be more negative than a pre-set value. It will be appreciated that this method could be enhanced by relating the acceptable value for holding current to the amplitude of the current in response to a voltage step.

Drug/Compound Application

The initial phase of drug application is unique to the interface patch clamp technique and involves the control of two single axis micromanipulators. The movements required utilize the position of the patch module micromanipulator recorded on entry into the interface as a reference point. After the cell has been immersed into solution contained in a perfusion chamber, the control logic calls a routine to carry out perfusion of the chamber via the activation of solenoid flow control valves.

Control Logic In Detail—(First Embodiment)

Variables/Parameters

Figure 8:
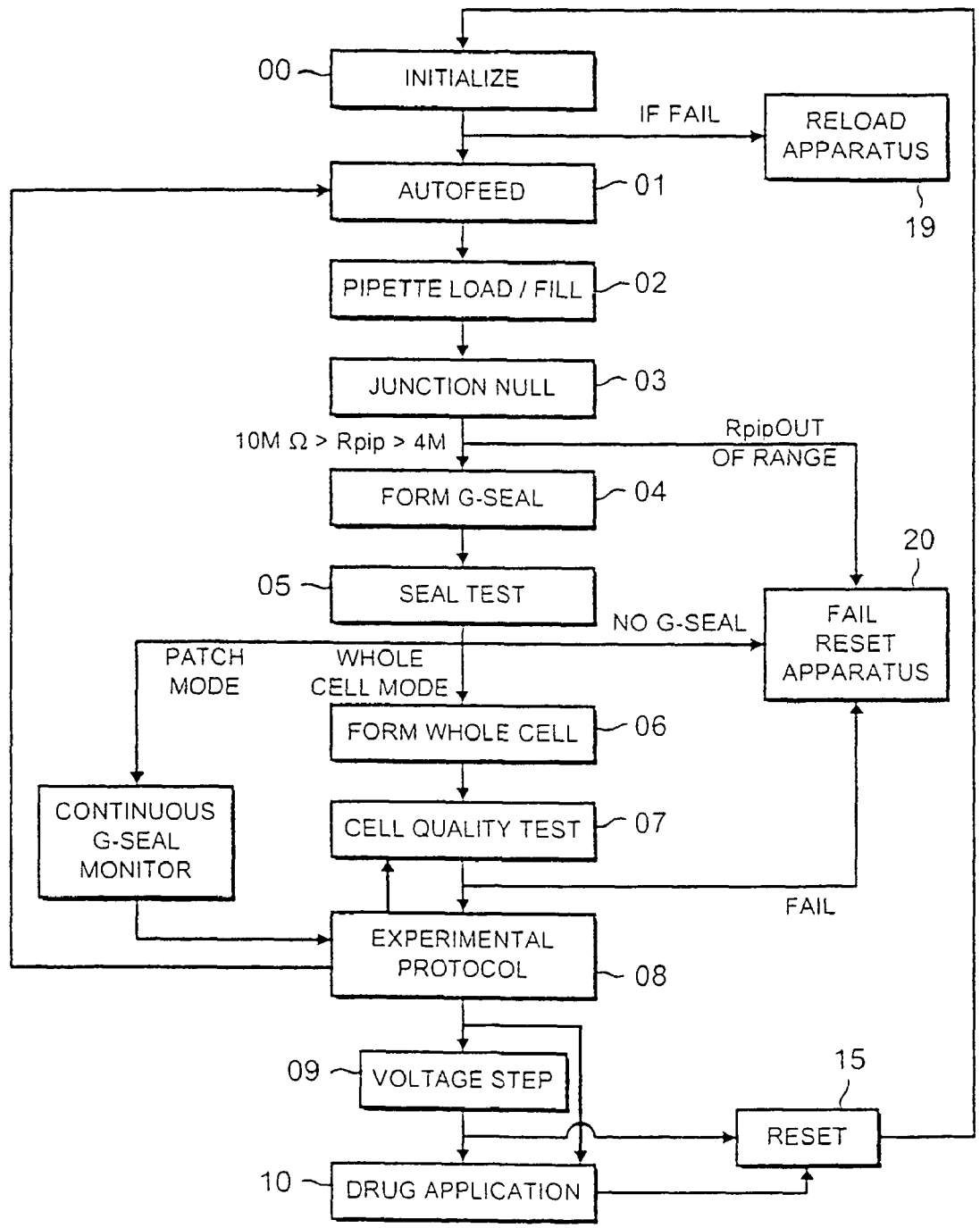
FIG. 8 is a flow diagram of control logic embodying a further aspect of the invention.

P=Pipette pressure relative to atmospheric pressure defined as 0
d=Patch module motor position
d0=Patch module motor start position
d1=Patch module motor position following entry of pipette into interface d2=Patch module motor position with pipette in recording position
d3=Patch module motor position for chamber perfusion
dapp=Drug application module micromanipulator position
dapp0=Drug application module micromanipulator position 0
dapp1=drug application micromanipulator position increment 1 Pre-set increment
dapp2=drug application micromanipulator position increment 2 Pre-set increment
Rs=Series resistance
Cslow=Slow capacitance compensation
Cfast=Fast capacitance compensation
lnoise=base line noise
Rpip=pipette resistance
Rtot=Total resistance
R1 Initial seal resistance (pre$_{set}$ value)
R2 Seal resistance required for progression to whole cell
Vhold=Pre set holding potential in mV
Imon=current monitor output
i=pre-set holding current
Ihold base line holding current for holding potential
dpip=pipette holder module motor position
dpip0=pipette holder module motor position start
dpip1=pipette holder module motor position pipette on
pclamp=position of pipette clamp/loader encoder
pclamp=0 pipette not clamped (loading position)
pclamp=1 pipette clamped (recording position)
rootclamp=position of rotary stage mounting for pipette loader
rotclamp=0 recording position
rotclamp=1 pipette filling position
pipfil=pipette filler position
pipefil=0 pre/post-fill position
pipefil=1 fill position
pipsyringe=pipette filler driven syringe position
pipsyringe=dv driven syringe movement required to fill pipette (pre-set value)
cclamp=position of capillary clamp/loader encoder
cclamp=0 capillary not clamped (loading position)
cclamp=1 capillary clamped (recording position)
pload=pipette loader empty signal
pload=0 pipettes in loader
pload=1 pipette loader empty
cload=capillary loader empty signal
cload=0 capillaries in loader
cload=1 capillary loader empty
celldiph=horizontal translator for cell dip
celldiph=0 cell storage encoder position (pre-set)
celldiph=1 dip encoder position (pre-set)
celldipv=verticle translator for cell dip
celldipv=0 pre/post-dip encoder positino (pre-set)
celldipv=1 capillary dip encoder position (pre-set)
tdelay=variable delay between clamping capillary and starting to patch clamp
dt=time interval
dt1=pre-set waiting time interval suction off (s)
dt2=pre-set suction time interval (s)
dt3=pre-set suction time interval (s)
dt4=pre-set suction time interval (s)
dt5=pre-set suction time interval (s)
x=suction increment factor
f=frequency of seal test pulse
detectmin=0−ve capacitance transient (3Inoise threshold) not detected
detectmin=1−ve capacitance transient (3Inoise threshold) detected
detectmax=0+ve capacitance transient (3Inoise threshold) not detected
detectmax=1+ve capacitance transient (3Inoise threshold) detected
I=Whole cell mode flag
I=0 Not whole cell
I=1 Whole cell mode established
singlem V=pre-set voltage test pulse
curr=current recorded between pre-set cursors during voltage step
testcurr=pre-set value for current required to start experimental protocol
Valve 1-8=solenoid valves controlling supply of solution to perfusion dish
tv=time interval for valve activation (pre-set)
drain valve=controls suction supply to perfusion dish Control Logic—Second Embodiment Control logic according to a further embodiment is illustrated as a flow diagram in FIG. 8. Exemplary logic steps within each of the functions shown in the flow diagram are set out below.

00 Initialization
d=d0
dpip=dpip0
pclamp=0
pipfil=0
rotclamp=0
cclamp=0
celldiph=0
dapp=dapp0
Rtot>/=20M
Imon=Inoise
P=0
If pload=0 and cload=0 then GOTO 01
If pload=1 then report "Re-load pipette cassette" and GOTO 19
If cload=1 then report "Re-load capillary cassette" and GOTO 19

01 Autofeed
Move capillary clamp motor cclamp=1
Move celldiph translator to celldiph=1
Move celldipv translator to celldipv=1
Move celldipv translator to celldipv=0
Move celldipv translator to celldiph=0
start timer
wait for variable delay=tdelay
GOTO 02

02 Pipette load/fill
Move pipette clamp motor pclamp=1
Move rotation stage 180 degrees rotclamp=1
move pipfil until pipfil=1
move motor driven syringe drive until pipsyringe=dv
move pipfil until pipfil=0
move rotation stage 180 degrees rotclamp=0
move dpip=dpip1
GOTO 03

03 Junction null
Seal test signal on
Compensate Cfast
Move patch module down until Imon>/<Inoise
Record patch module motor position d=d1
Activate Junction null
Measure Rtot Rtot=Rpip
If Rpip <10 M and >/=4 M GOTO 04 else Report "Pipette resistance out of range" and GOTO 20

04 Formation of Gseal
Measure Rtot
If Rtot=/>2Rpip
Suction on P=−pmmHg
Move patch module down until d=d2
(d2=pre-set recording position)
GOTO 05
04.1
If Rtot<2 Rpip
Wait for time t1
After time t1 move patch module upwards until Rtot>2Rpip then stop. Wait until
Rtot=2Rpip then move patch module down until d=d1
If d=d1 and Rtot=/>2Rpip then suction on P=−pmmHg and move patch motor module down until d=d2, else GOTO 04.1 until maximum of 5 iterations, then GOTO 20

05 Seal test loop
05.1 N=N+1
Measure Rtot with −pmmHg for time interval delta t2
If Rtot>/=R1 and dt</=dt2
Then suction off P=P0 until Rtot=/>R2 or dt=t1
If Rtot<R1 and dt>t1
Then repeat 05.1 until N=5 or Rtot=/>R2
If N=5 and Rtoto<R2 Then suction on−xpmmHg
Repeat 05.1. until N=5 or Rtot=/>R2
If N=5 and Rtot<R2 Then suction on−xpmmHg
Repeat 05.1 until N=5 or Rtot=/>R2 or x=pmax
If x=pmax and Rtot<R2 Then Report "Unable to obtain G seal" GOTO20
If Rtot=/>R2 then GOTO 06 for Whole Cell Mode or GOTO 08 for Cell Attached Patch Mode

06 Whole Cell—Threshold Method
Compensate Cfast
I=0
hp=vhold
06.1 Suction on−pmmHg until I=1 or dt=dt3
06.2 Transient detection
N=N+1
If detectmax=1 and detectmin=1
Then I=1
Repeat 06.2 until detectmax=0 and detectmin=0 or N=10
If N=10 Then GOTO 07
If detectmax=0 and detectmin=0
Then GOTO 06.1

07 Cell quality test
Measure Rs and Ihold
if Rs=/>3Rpip Suction on−pmmHg and start timer
When Rs<3Rpip suction off
If Ihold<ipA then and Rs<3Rpip then seal test signal off and GOTO 08
If hold>ipA and time int=dt4 then GOTO 20
If Rs=/>3Rpip and time int=dt5 then suction on −pmmHg
If Rs=>3Rpip and Ihold<ipA then seal test signal off and GOTO 08

08 Experimental protocol
Apply single voltage step to singlemV
Measure current amp during voltage steps
If curr<testcurr then stop voltage steps
Report "Control current out of range"
GOTO 15
If curr=/>testcurr activate voltage step protocol GOTO 09
Measure Rs
If Rs=/>3Rpip stop voltage protocol and GOTO 07
Measure Ihold during interval between voltage steps
If Ihold>ipA then stop voltage step/drug application protocol and GOTO 01

09 Voltage step protocol
Uses program already available
Program must call drug application sub-routine 10

10 Drug/compound application
drain valve on
Fill drug application chamber Valve1 on for time interval
Move drug application micromanipulator down to d1 −dappl1 (NB−ve value represents downward movement)
Move dapp=d1+dapp2 and d=d2+dapp2 simultaneously move d=d3 glass capillary moved up
Call software controlling flow control valves

15 Reset Autopatch
GOTO 00

19, 20 Steps 16 onwards are routines for setting up the apparatus controlled by the software/method and do not relate to the inventive operation of the apparatus and their design is within the normal competency of the skilled person. Steps 19 and 20 relate respectively to reloading the pipette and capillary cassettes and to checking and/or resetting of the apparatus if operation is unsuccessful.

Figure 9:
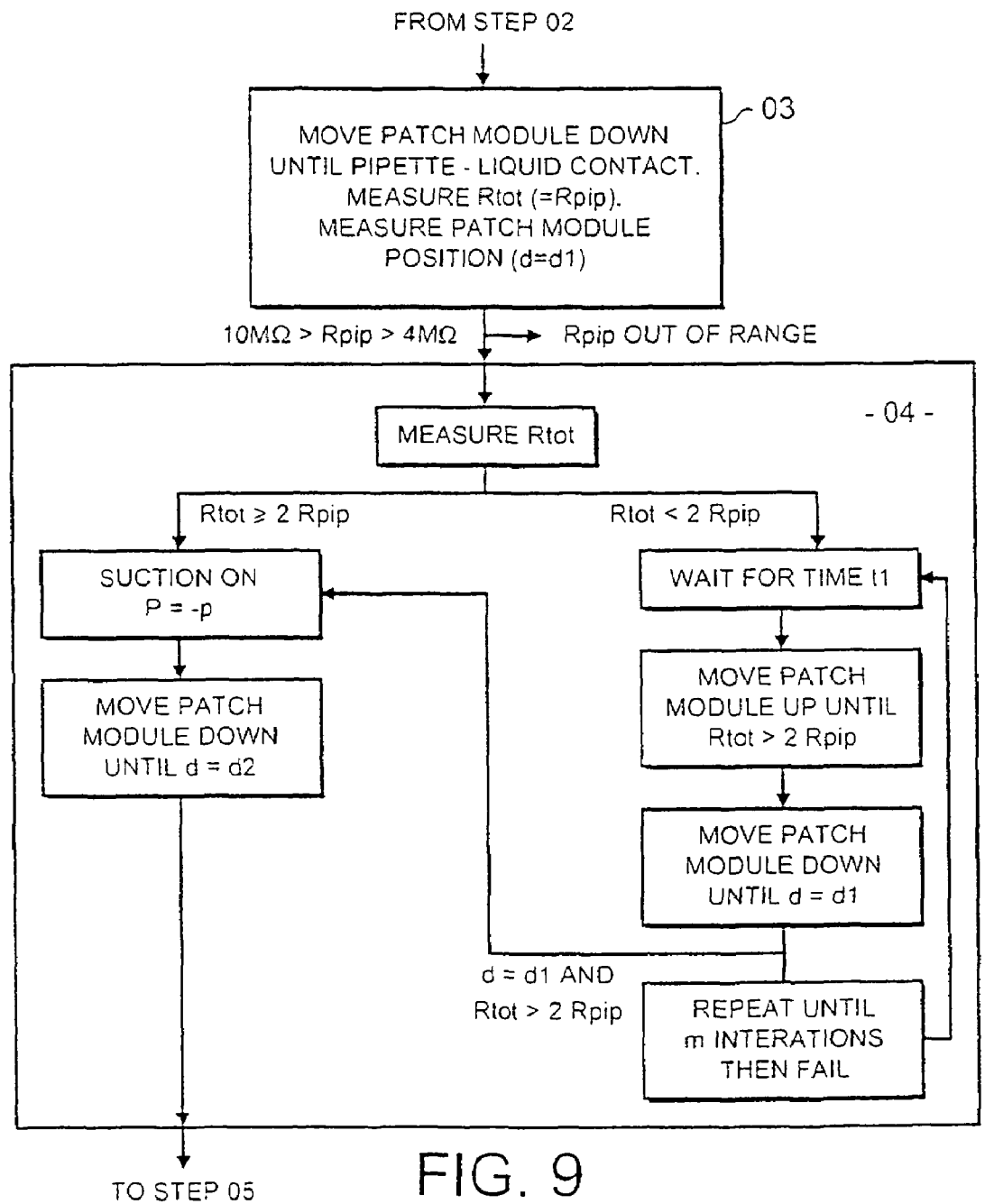
FIG. 9 is a flow diagram of an example of the G-seal formation steps of FIG. 8.

FIG. 9 is a flow diagram illustrating steps 03 and 04, which relate to formation of the G-seal. These steps comprise the most important advantageous steps in this embodiment for controlling the method and apparatus described herein.

In step 03 (junction null), the pipette tip is initially spaced below the meniscus at the end of the capillary. The logic, or software, then controls the patch module motor to move the pipette tip towards the meniscus until contact is made, detected by electrical contact therebetween. The movement is then stopped while the pipette resistance is measured and the motor position recorded (d=d1, as shown in FIGS. 1*b* and 3). If Rtot is outside a predetermined range, the experiment is aborted.

In step 04, Rtot is measured and if it is above a predetermined threshold, it is assumed that a cell is positioned on the pipette tip so suction is applied to the pipette and the logic controls the patch module motor to move the pipette tip further into the liquid within the capillary to a predetermined recording position (d=d2, as shown in FIGS. 1*b* and 3). The logic then moves to step 05 to test the G-seal.

If at the start of step 04, Rtot is less than the predetermined threshold, the logic assumes that there is no cell at the pipette tip. The logic then waits for a predetermined time interval t1 before controlling the patch module motor to move the capillary away from the pipette until Rtot is measured to be greater than the predetermined threshold, when the movement is stopped. It is believed that in this position the pipette tip is still in contact with the liquid in the capillary but only via a neck, or bridge, of liquid drawn out by surface tension between the capillary and the pipette. The logic then waits until Rtot drops to equal the predetermined threshold. The logic then controls the patch module motor to return the pipette tip to d=d1, the position when it first contacted the capillary meniscus in step 03. If Rtot is then greater than the predetermined threshold it is assumed that contact with a cell has been made at the pipette tip, suction is applied to the pipette and the logic controls the patch module motor to move the pipette into the capillary to the predetermined recording position at d=d2. It is believed that waiting for the time interval t1, which may be between 0.5 and 10 seconds, or preferably about 1 to 5 seconds, permits movement of the cells at the capillary tip, which is encouraged by the movement of the pipette tip to draw out the capillary meniscus.

If Rtot is still less than the predetermined threshold, the steps of waiting for time t1 and slightly moving the pipette are repeated for a predetermined number of iterations until a failure condition (step 20) is reached.

Control Logic—Third Embodiment

FIGS. 10 to 16 are flow charts illustrating a third embodiment of the control logic of the invention. Aspects of the third embodiment are, where appropriate, common to the first and second embodiments. The third embodiment, however, incorporates certain improvements resulting from experiments by the inventor.

Figure 10:
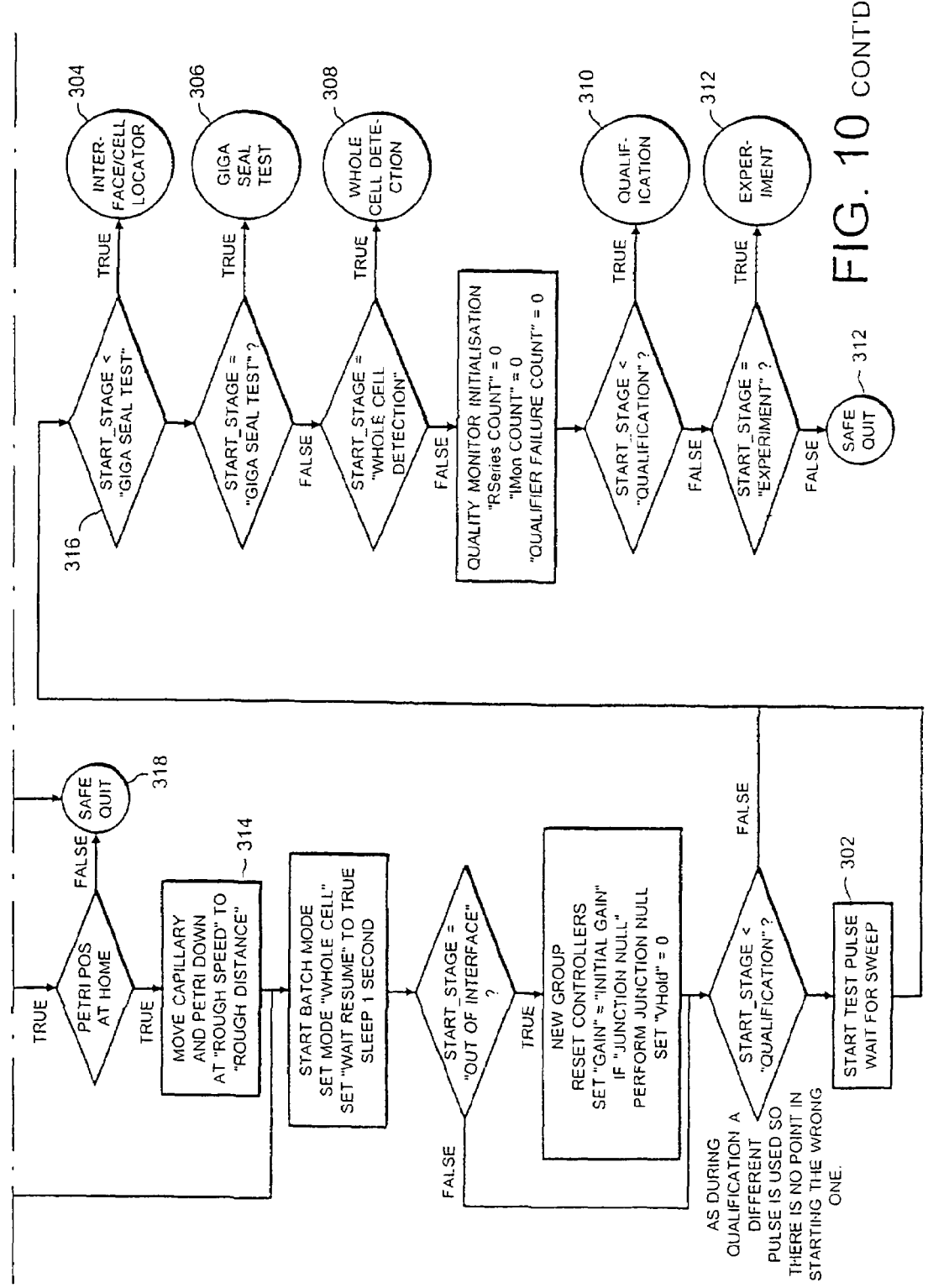

FIG. 10 is a flow chart showing all of the operations of the control logic, or software. This is termed the AutoPatch system. FIGS. 11 to 16, and FIGS. 10*a*, 10*b*, 11*a*, 16*a* and 16*b*, are expanded flow charts for operations within the flow chart of FIG. 10.

FIG. 10 describes the setting up of the AutoPatch system, including the initialization of all the relevant hardware. This involves the steps up to starting the test sweep 302, after which the steps of interface or cell location 304, Giga seal testing 306, whole cell detection 308, qualification 310 and experiment 312 are performed as described herein. Note that during the patching process, the movements of the capillary and the petri dish are locked together by the software in order to maintain their positions relative to each other constant. The movement of the petri dish has no role in the patching process.

Initially the capillary and petri dish move towards the pipette at a rapid speed to a pre-set distant (step 314) in order to position the liquid/air interface within approximately 1 mm of the pipette tip. This initial (rough) position is performed in order to shorten the time interval between starting the patching process and reaching the interface. The distance between the patch pipette tip and the liquid/air interface is initially larger than 1 mm in order to allow sufficient space for loading of the pipette and the capillary. After rough positioning, the seal test pulse is started (step 316) and the translators (capillary and petri dish) are switched to slow speed prior to entry of the pipette into the liquid/air interface.

FIGS. 10*a* and 10*b* expand the safe quit routine 318 and the reset routine 320 used at various points by the control logic or software.

Figure 11:
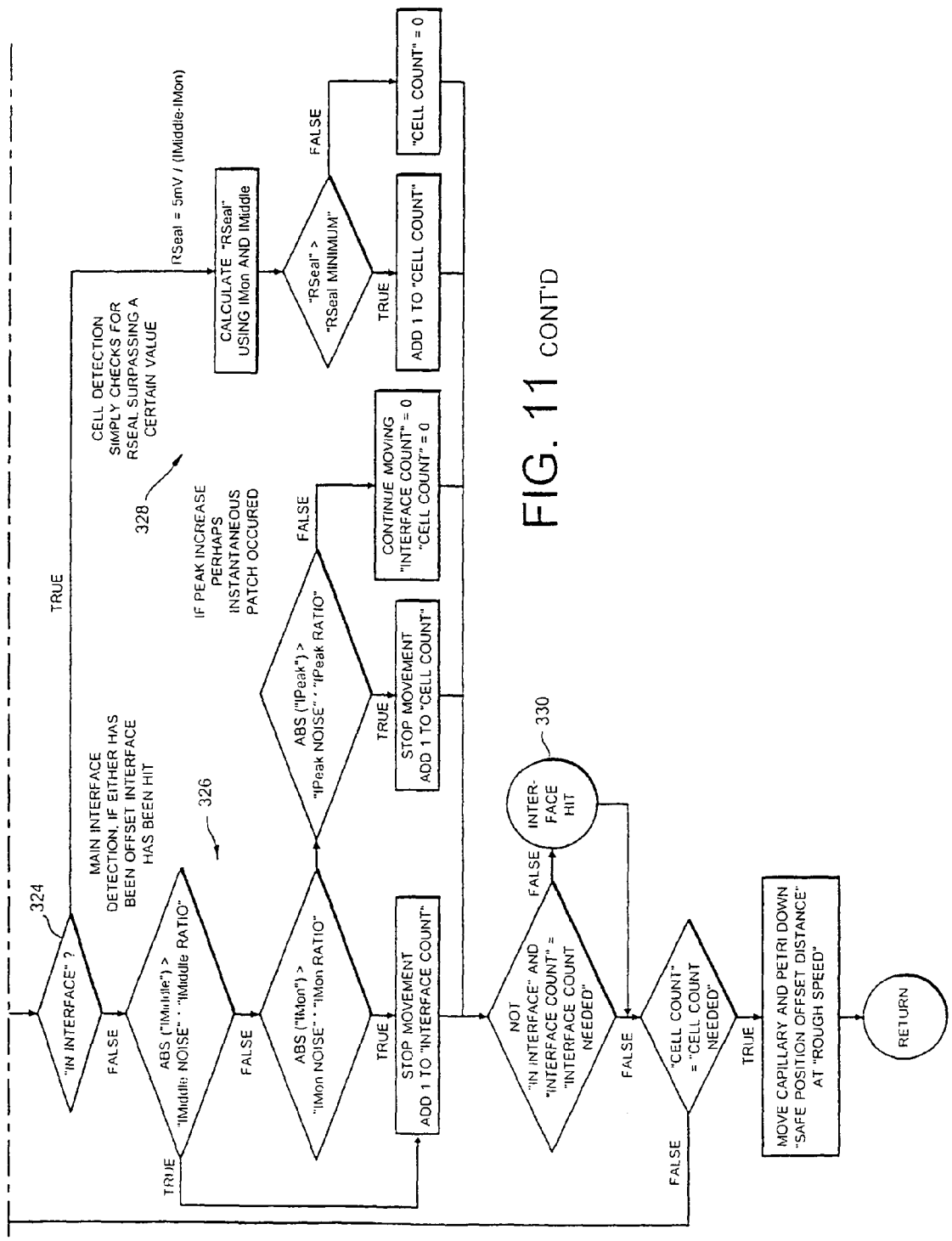

FIG. 11 is a flow diagram expanding the interface or cell locator routine 304 of FIG. 10. In this routine, suction is applied to the interior of the pipette, and the capillary and petri dish are moved towards the pipette at a slow rate (e.g. 10 micrometers/s) (step 322). The current is monitored after each sweep to determine when the interface is detected (step 324). The interface is detected by an offset in the baseline current or the appearance of a current pulse when the circuit is made 326. In contrast with conventional patch clamp, seal formation with the Interface Patch Clamp technique can occur virtually simultaneously with contact between the pipette tip and the external bathing solution at the interface 328. The logic distinguishes between an open circuit (pipette tip in air) and a rapidly formed seal by monitoring the current trace for the appearance of a capacitance transient at the end of the seal test pulse )step 326). This transient is due to the pipette capacitance, which increases as the pipette is immersed into the solution at the interface. As the pipette tip touches or crosses the air/liquid interface the capacitance is likely to be undetectable amongst electrical noise. As the pipette tip moves into the liquid, however, the capacitance increases until it is detectable over the noise.

After the pipette has entered the interface, the capillary (and movement of the petri dish) is stopped, a junction null may be performed and the pipette resistance is monitored. The presence of a cell on the pipette tip is indicated by an increase in pipette resistance which must reach a pre-set value before the logic will allow the system to proceed to the next step. After a cell has been detected the Giga seal test 306 is undertake.

FIG. 11*a* expands the interface hit routine 330 of the interface or cell location routine 304 of FIG. 11.

Figure 12:
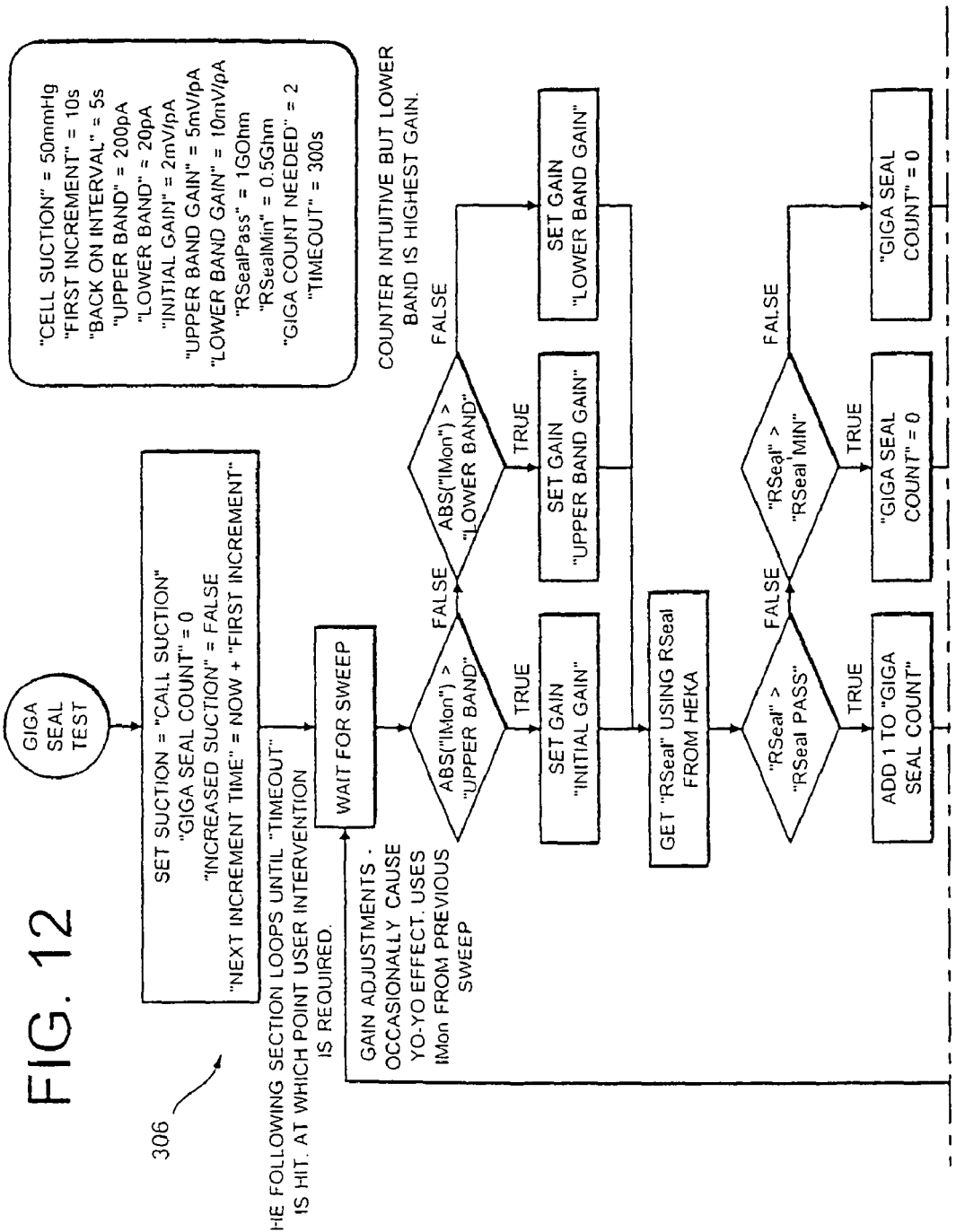
Figure 12:
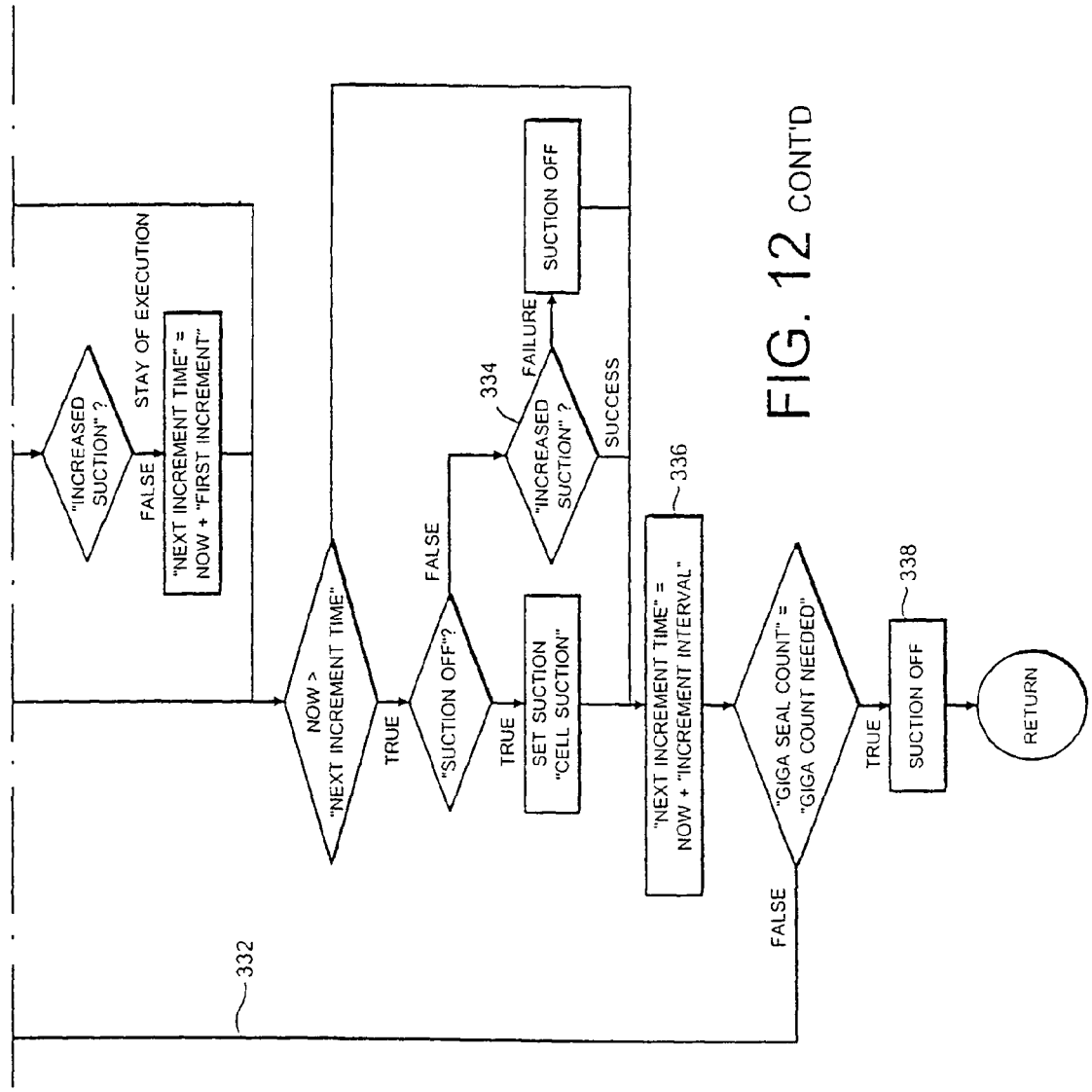

FIG. 12 is a flow diagram of the Giga seal test routine 305 carried out after contact with a cell has been detected in the interface or cell location routine 304. The Giga seal test routine 306 comprises a repetitive loop 332 in which the level of suction applied to the pipette interior is increased in pre-set increments 334 and times 336 while monitoring the change in pipette resistance. The suction is increased until the maximum vacuum is obtained or Giga seal formation occurs. The loop ends and the suction is switched off 338 if either of these conditions is satisfied. If the maximum suction has been applied but a Giga seal has not formed the loop is repeated until Giga seal formation or time-out. The formation of a Giga ohm seal is required in order to allow progression to the next stage.

Figure 13:
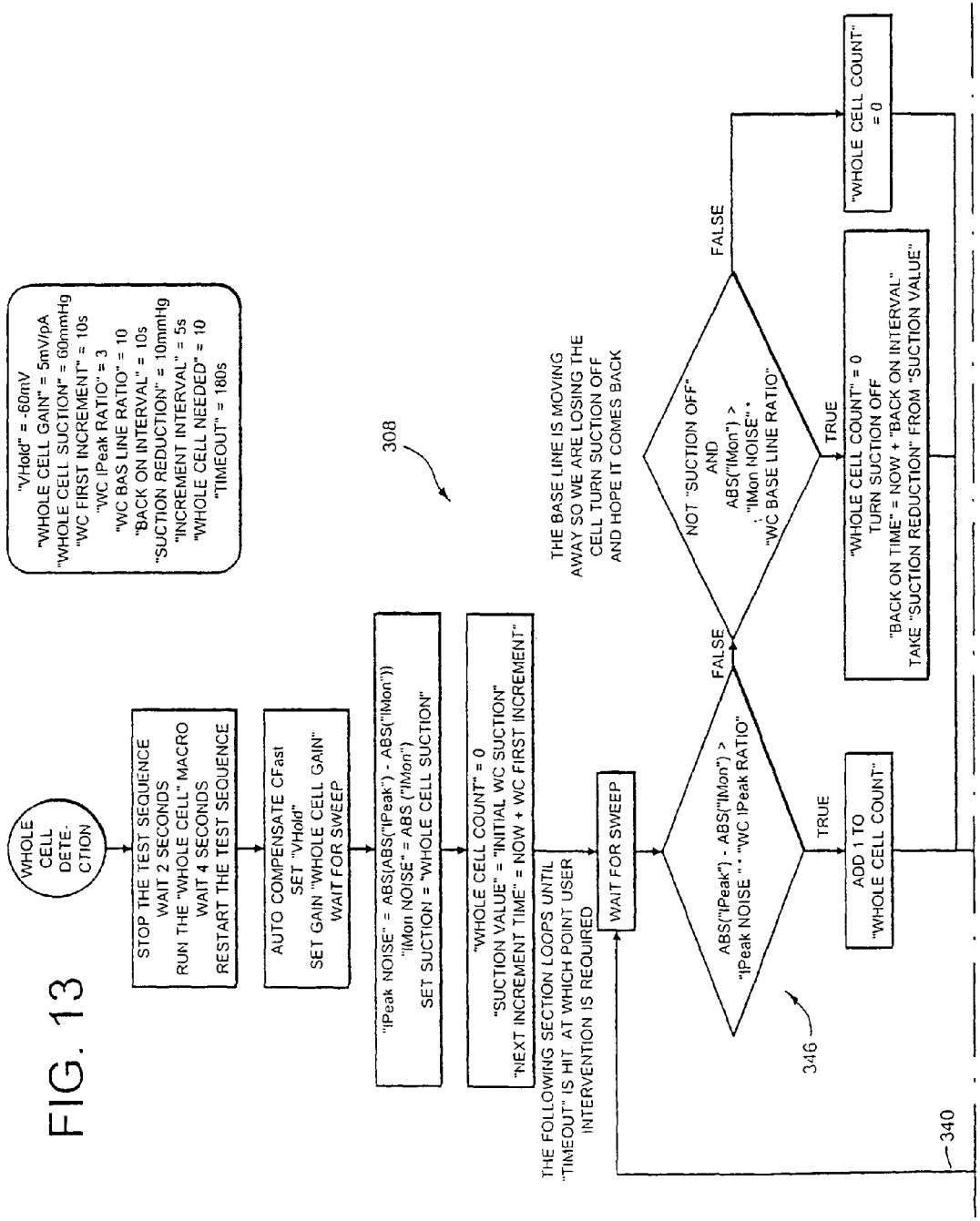
Figure 13:
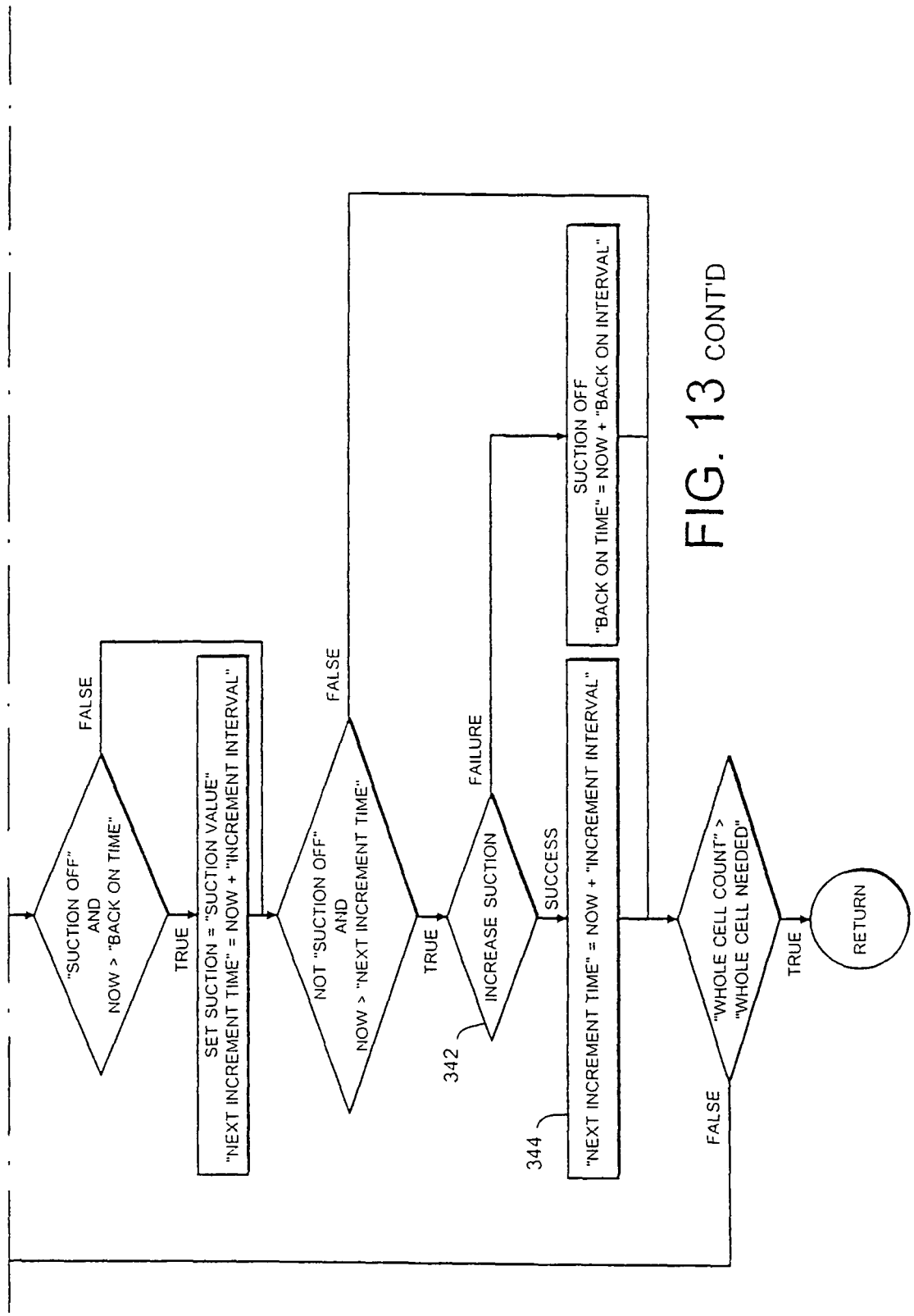

FIG. 13 expands the whole cell detection routine 308 of FIG. 10. In this routine, the transients due to the pipette capacitance are cancelled and this is followed by a repetitive loop 340 in which the level of suction applied to the pipette interior is increased in pre-set increments 342 and times 344 while monitoring the current 346 for the appearance of capacitance transients. These transients are due to the charge and discharge of the cell membrane capacitance and are indicative of the formation of whole cell recording mode.

Figure 14:
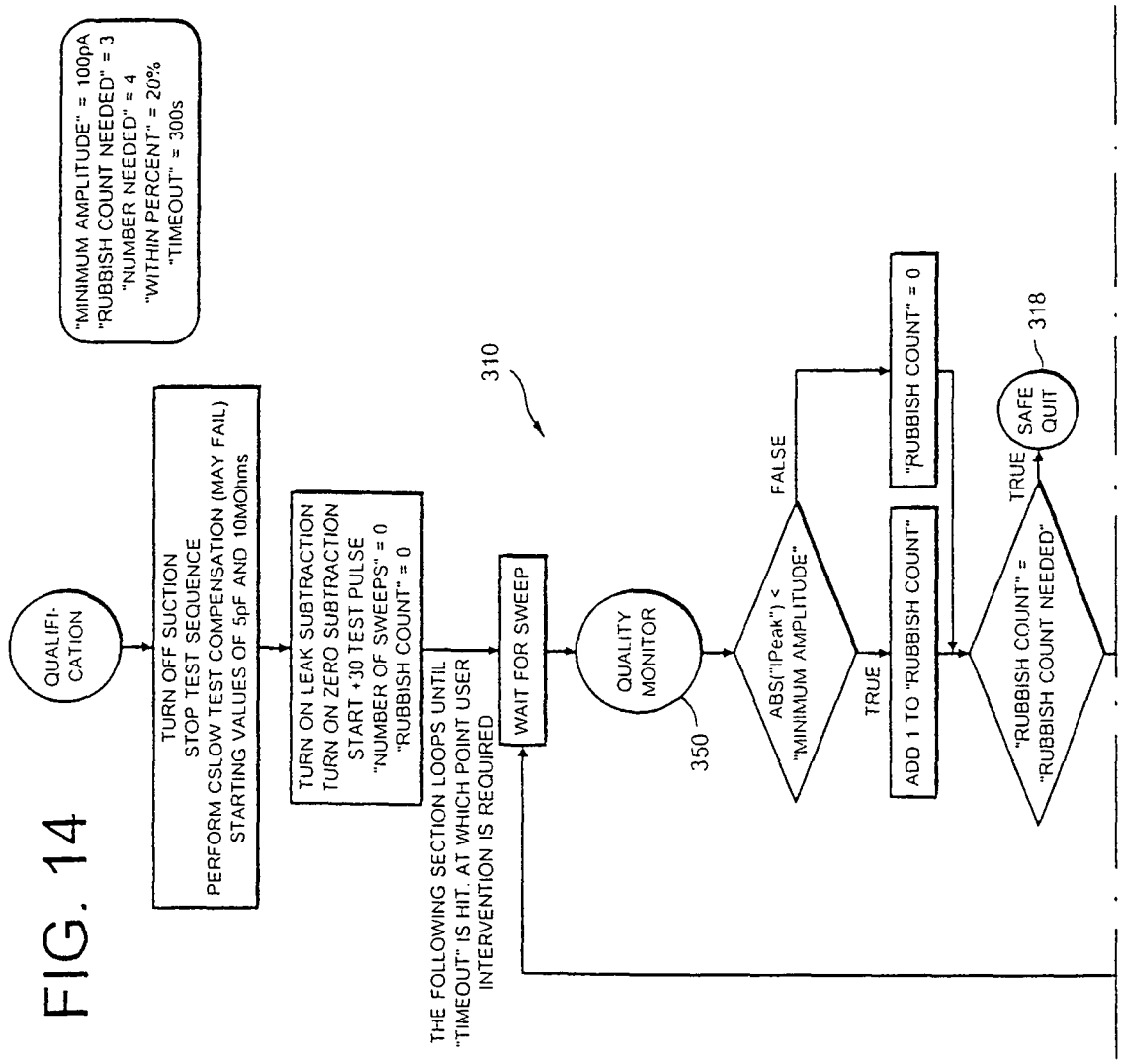

FIG. 14 expands the qualification routine 310 of FIG. 10. In order to qualify for use in an experiment the cell must exhibit a voltage gated (or other) current equal to or greater than a pre-determined amplitude and polarity 348 in response to a test pulse. Qualification proceeds until the cell qualifies or timeout is hit. During qualification the quality monitor 350 is run also.

Figure 15:
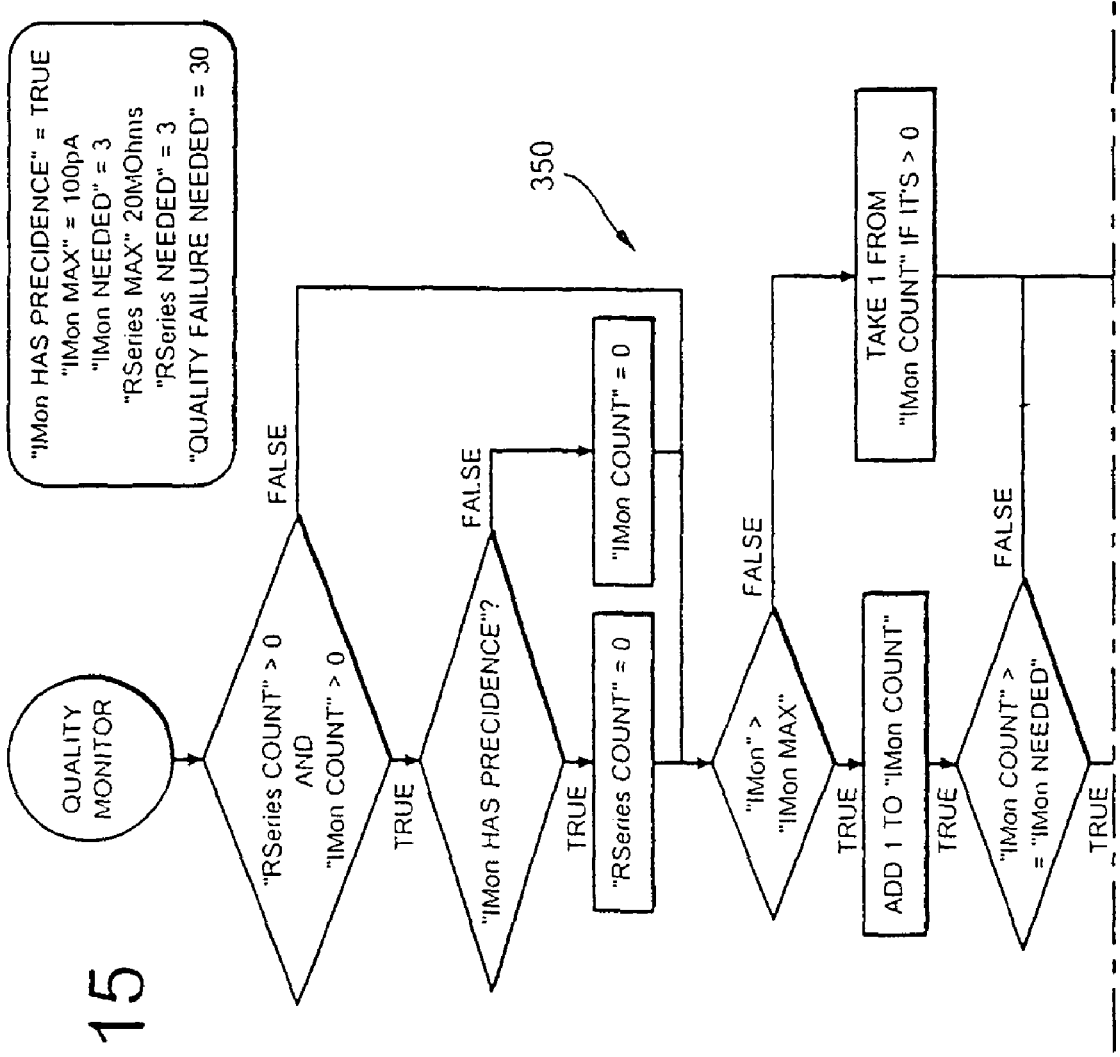
Figure 15:
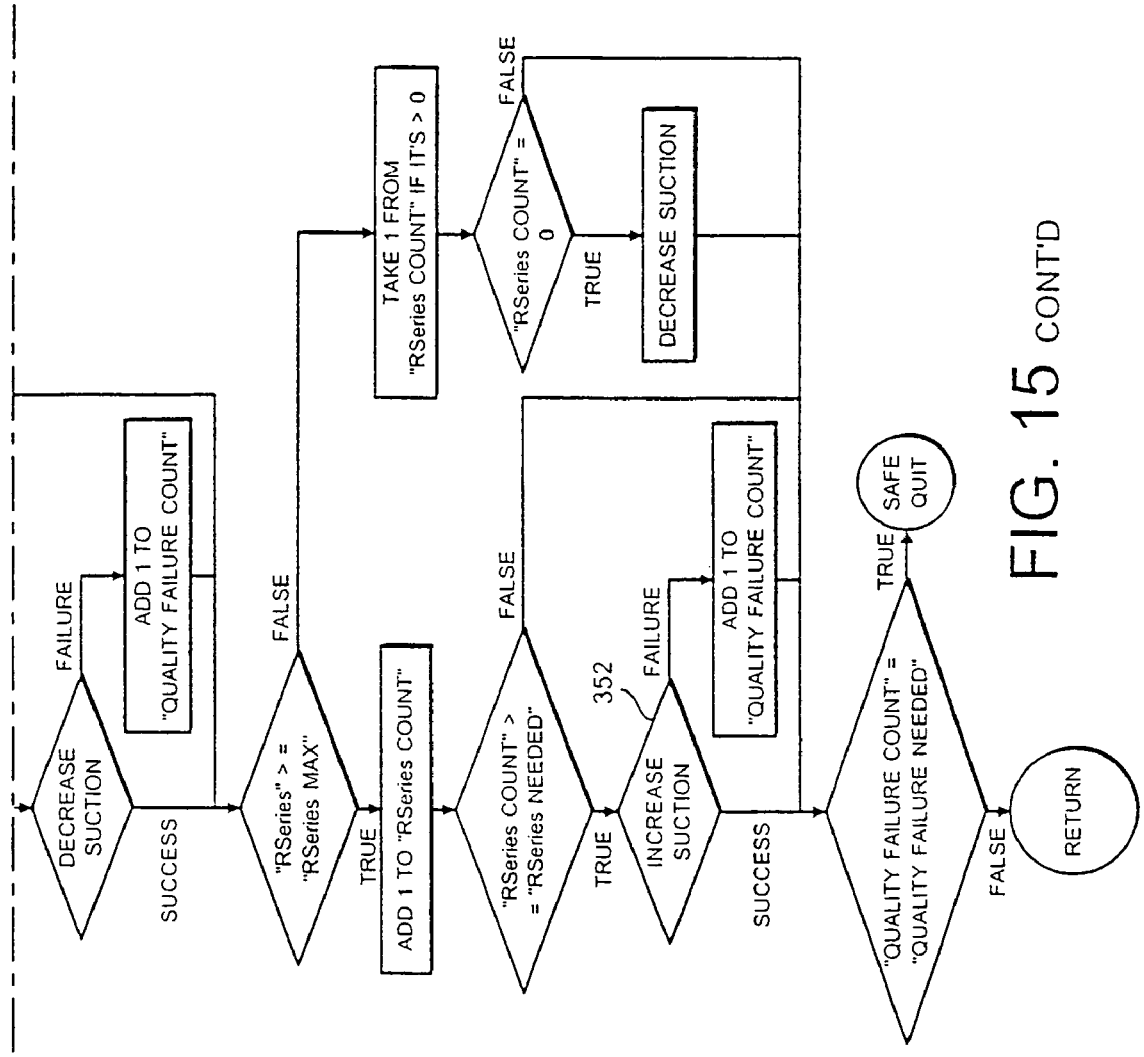

FIG. 15 is a flow diagram of the quality monitor routine 350 of FIG. 14 and 16, described below. It comprises a repetitive loop in which the pipette suction is varied in response to measurements of series resistance (RSeries) and current (IMon). Current flow through the cell membrane via the pipette generates a voltage error due to RSeries. The value of RSeries often increases during whole cell recording and this effect can be reduced by the application of suction to the pipette interior 352. An increase in the value of the current at the holding potential (usually–60 mV) indicates loss of the Giga seal and this can be caused by excessive suction. Acceptable values for RSeries and IMon are entered in the settings for the software. The quality monitor runs both during the qualification stage and the experiment.

Figures 16, 16B:
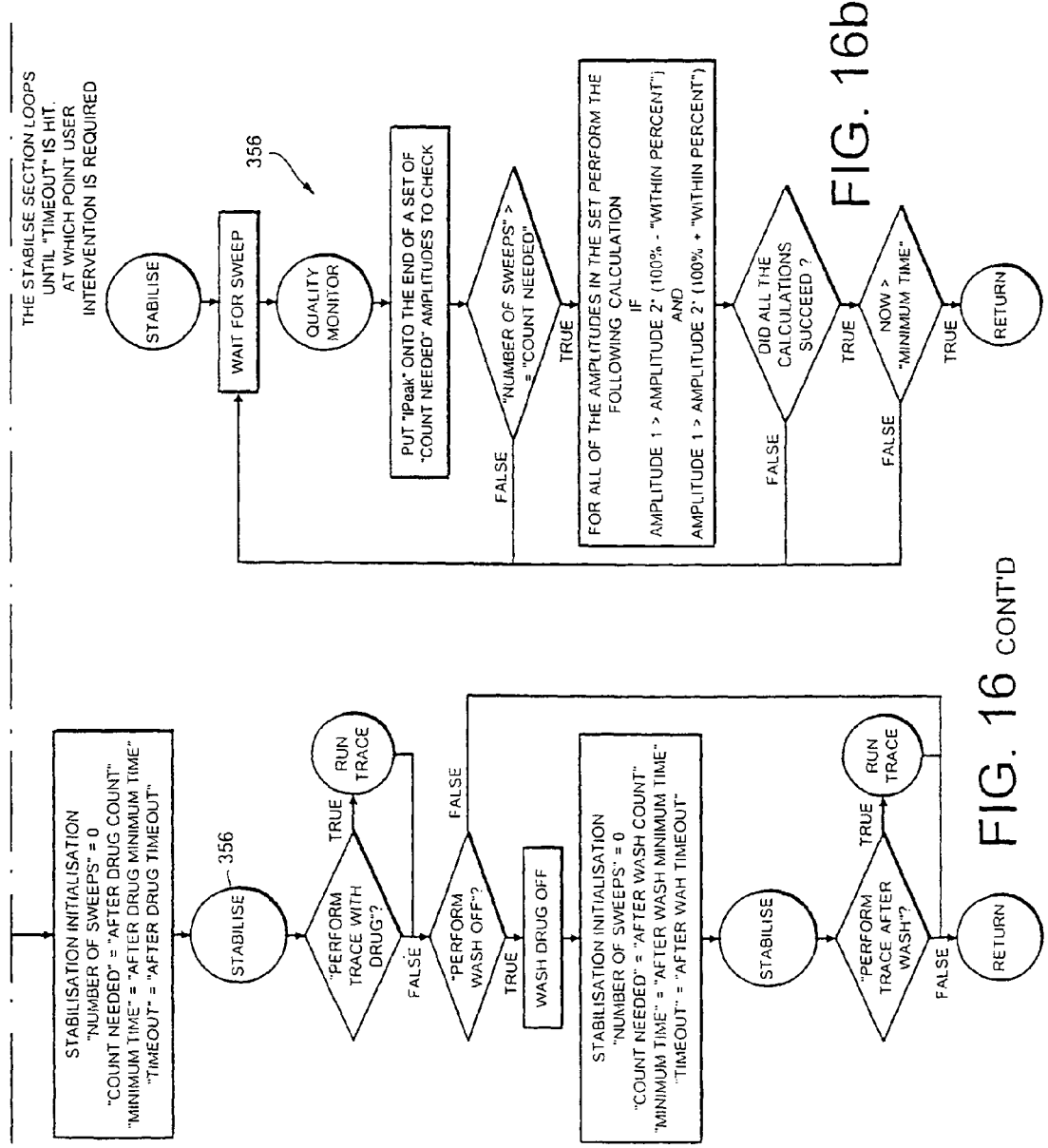

FIG. 16 expands the experiment routine 312 of FIG. 10. In the experiment routine, movements of the petri dish and capillary required to carry out drug application by the method shown in FIGS. 4-7 inclusive are carried out. During these movements the dish is filled with external solution/external solution plug drug via solenoid operated flow control values 358. Before drug is added, the current evoked by the test pulse (or pulses) must be reproducible within a pre-determined percentage (entered in the settings).

FIGS. 16a and 16b expand the trace run routine 354 and the stabilize routine 356 of the experiment routine 312.

Figure 17:
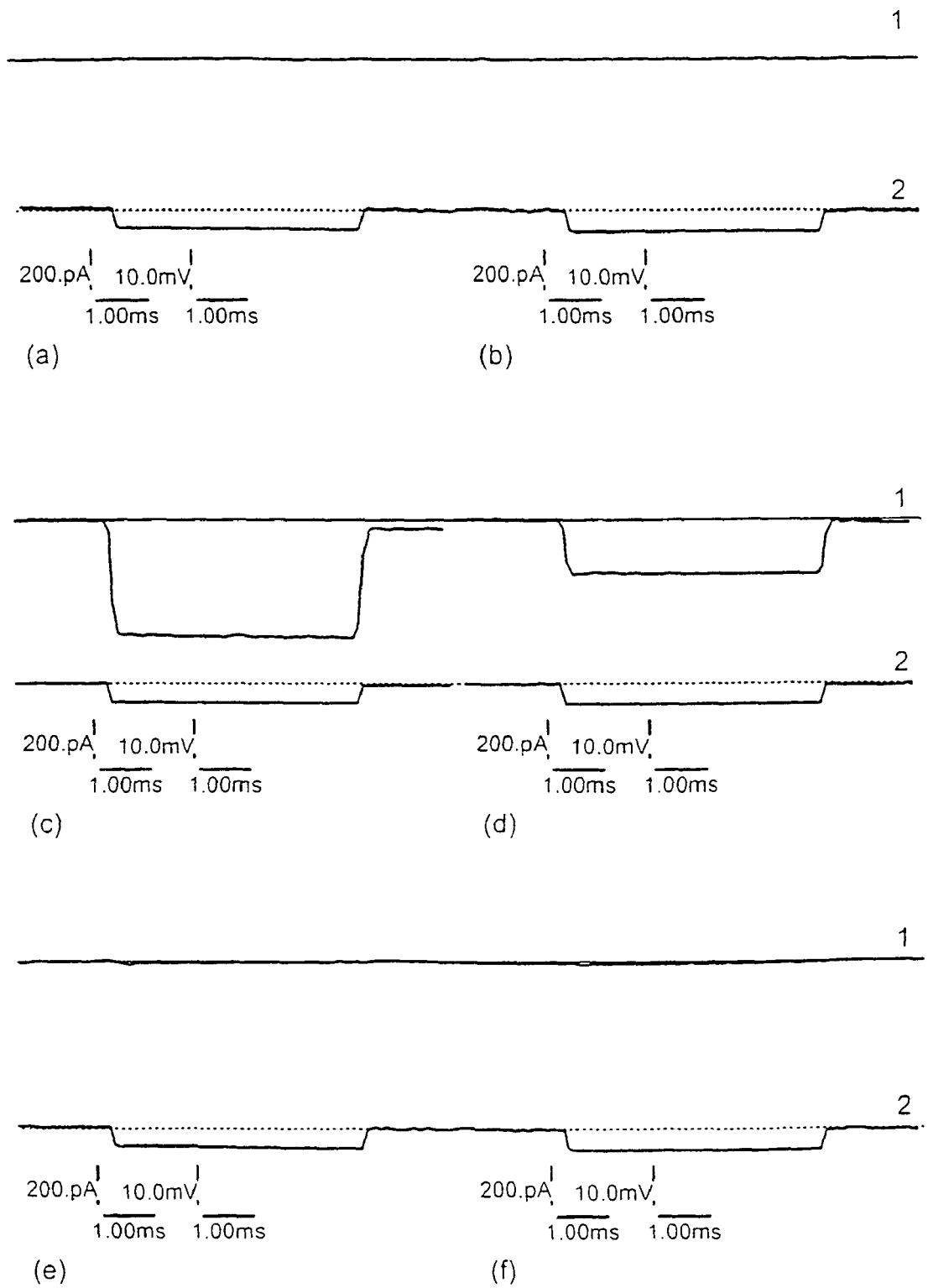

FIG. 17 shows recordings of current (1) and voltage (2) obtained from an automated patch clamp system (AutoPatch) showing the formation of a Giga Seal under software control using the Interface Patch Clamp technique. Recordings from an MK1 cell.

FIG. 18 shows recordings of current (1) and voltage (2) from an automated interface patch clamp system (AutoPatch) showing the increase in capacitance transient observed after moving the capillary to position d2 (records a and b). (c) and (d) were obtained after automatic compensation for pipette capacitance and a change in the holding potential to −60 mV. Recording obtained from the same cell as FIG. 17.

FIG. 19 shows recordings of current (1) and voltage (2) from an automated interface patch clamp system (Auto-Patch). Records (a) and (b) were obtained after Giga seal formation (cell attached patch mode) using the interface patch clamp technique. The application of suction to the pipette interior under full software control ruptured the membrane patch to obtain the whole cell recordings shown in (c) and (d). The establishment of the whole cell mode of recording is shown by the presence of the large capacitance transients on the current trace. Recording obtained from the same cell as FIGS. 17 and 18.

FIG. 20 shows recordings of membrane current (1) and voltage (2) in whole cell recording mode obtained using an automated patch clamp system (AutoPatch) which employs the interface patch clamp technique. The holding potential was −60 mV and (a) and (b) show outward potassium currents (Kv1.1) in response to a voltage step to +30 mV. Recording obtained from the same cell as FIGS. 17, 18 and 19.

FIG. 21 shows the effect of the potassium channel blocking drug tetraethylammonium (TEA) on the potassium current recorded from MK1 cell in whole cell recording mode obtained using the Interface Patch Clamp technique. After the establishment of whole cell recording mode the cell was positioned in a recording dish by the method shown in FIGS. 4 to 7 and described in the text.

(a) shows the current obtained in normal extracellular solution (b) shows the effect of replacing the solution in the dish with extracellular solution containing TEA (5 mM).

(c) the blocking effect of TEA was reversed by washing.

It will be readily appreciated by those skilled in the art that:

1. The stability of recording using the interface patch clamp technique may be superior to that of conventional patch clamping. The greater stability of interface patch clamping is because the cell is held by the patch pipette alone. In conventional patch clamp recordings the cell is held by the path pipette and a solid substrate and vibration tends to move the pipette relative to the substrate causing loss of the G-seal. The interface patch clamp is, in contrast to conventional patch clamp apparatus, relatively insensitive to vibration during drug application.
2. This method of drug application could be applied to a plurality of recording pipettes/capillaries and form the basis for a high throughput electrophysiological assay system. It will readily be appreciated that the Interface Patch Clamp technique could be used with multiple pipettes and multiple capillaries in a manner in which each pipette enters its respective aligned capillary either individually in sequence or all together. Although not currently preferred, a single pipette could be used which is caused to enter more than one capillary sequentially. Multiple patch clamp recordings could be made either sequentially or simultaneously, depending on the application.

Figure 22:
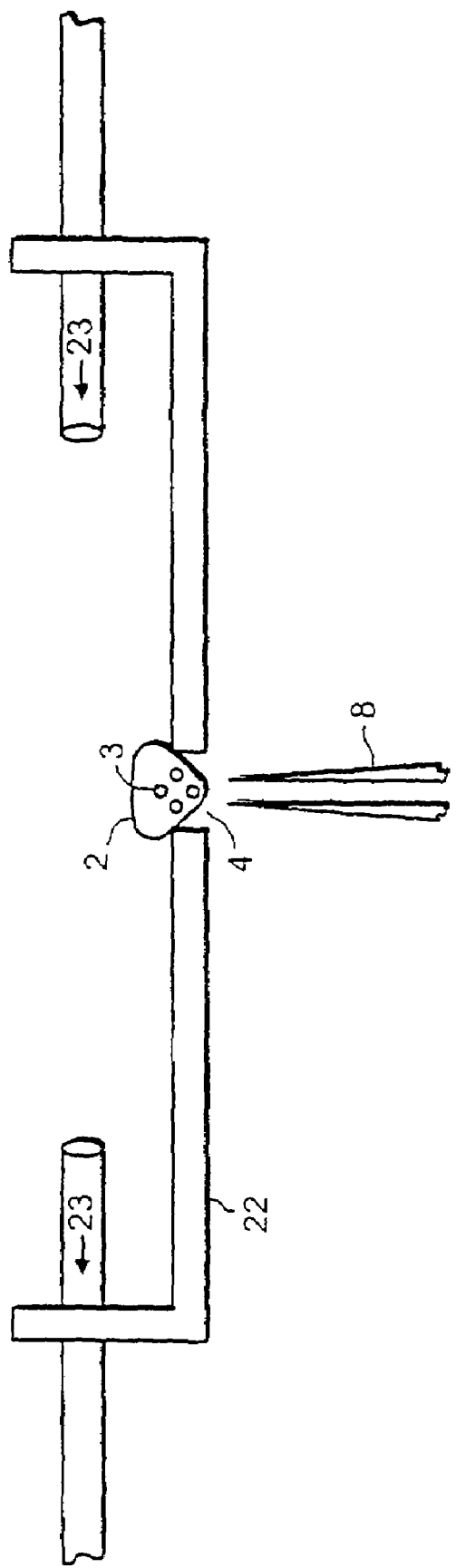
FIG. 22 shows cells suspended in a droplet of liquid covering a hole through a support surface and providing an air/liquid interface according to the invention.

As was mentioned above, it is not essential to the general principle of the invention to use a capillary in order to create a column of liquid which gives rise to a liquid/air interface at which cells can be located. Other ways can be envisaged in which the same effect can be achieved. For example, as shown in FIG. 22, a droplet or "blob" of liquid may be provided on a support surface. The surface has a hole through it and the droplet covers the hole. Surface tension prevents the liquid from the droplet dropping through the hole. Within the droplet cells are suspended. This allows access to the droplet and the cells contained therein by a suitable electrode such as a patch pipette. In the arrangement shown in FIG. 22, means are provided for flow of other liquids in to and out of a dish or other container of which the support surface with the hole in it forms a wall. Once a cell has been attached to the electrode, other liquids may be introduced into the container either in batch mode or in flow-through mode in order to result in the cell being exposed at its external surface to the surrounding liquid. Clearly in such an arrangement, the original liquid and the remaining un-attached cells will tend to be washed away from the area of the electrode/pipette.

Figure 23:
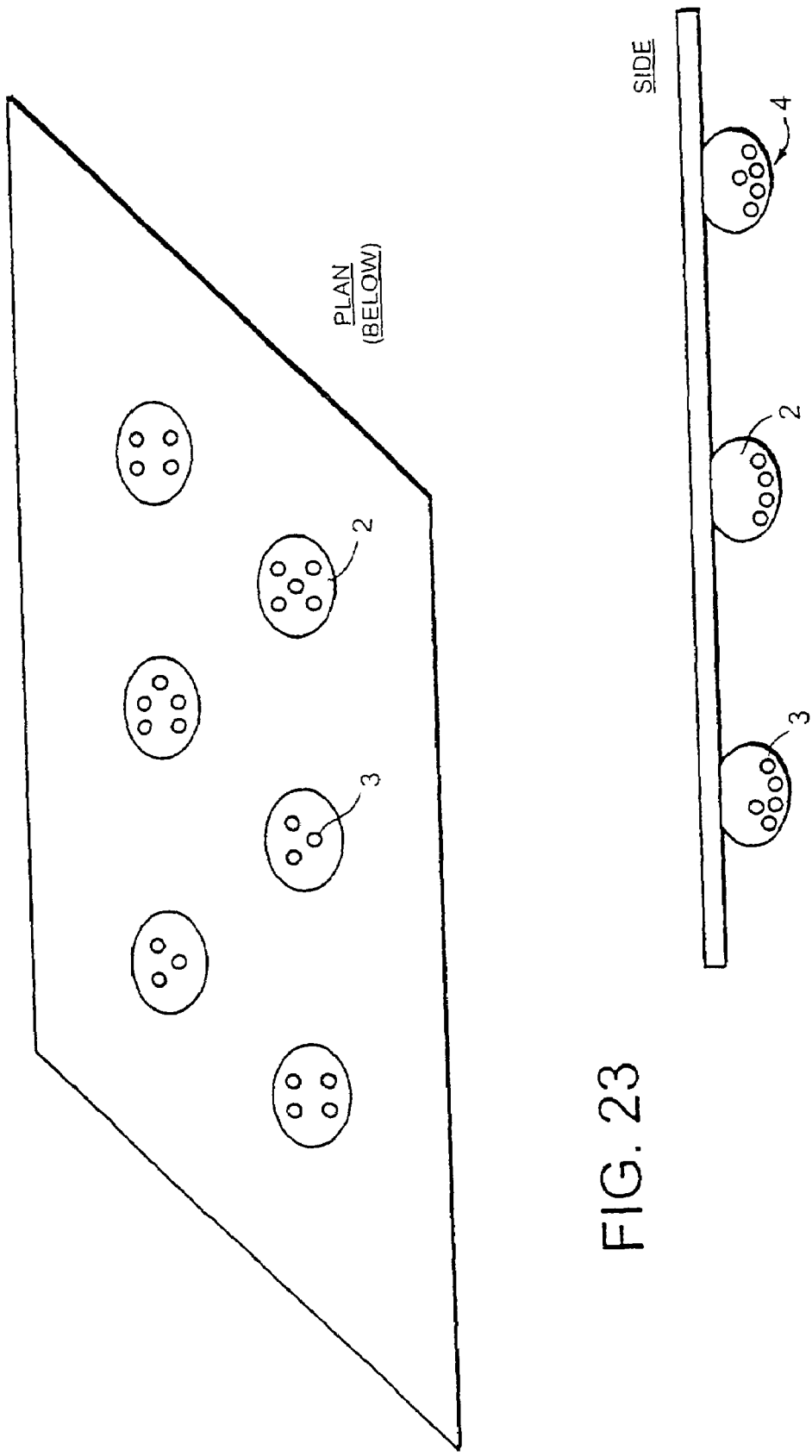
FIG. 23 shows a further embodiment of droplets containing cell suspensions forming air/liquid interfaces according to the invention.

It is within the scope of the invention that droplets might be provided on non-perforate support surfaces. As shown in FIG. 23, the effect of surface tension may be to allow droplets of a suitable liquid to adhere automatically to the underside of a suitable support surface. The support surface might for example be a cover slip of glass or other material. Droplets in which cells are suspended provide the air/liquid interface according to the invention and consequently may be used in a method of interface patch clamping as described above.

Figure 24:
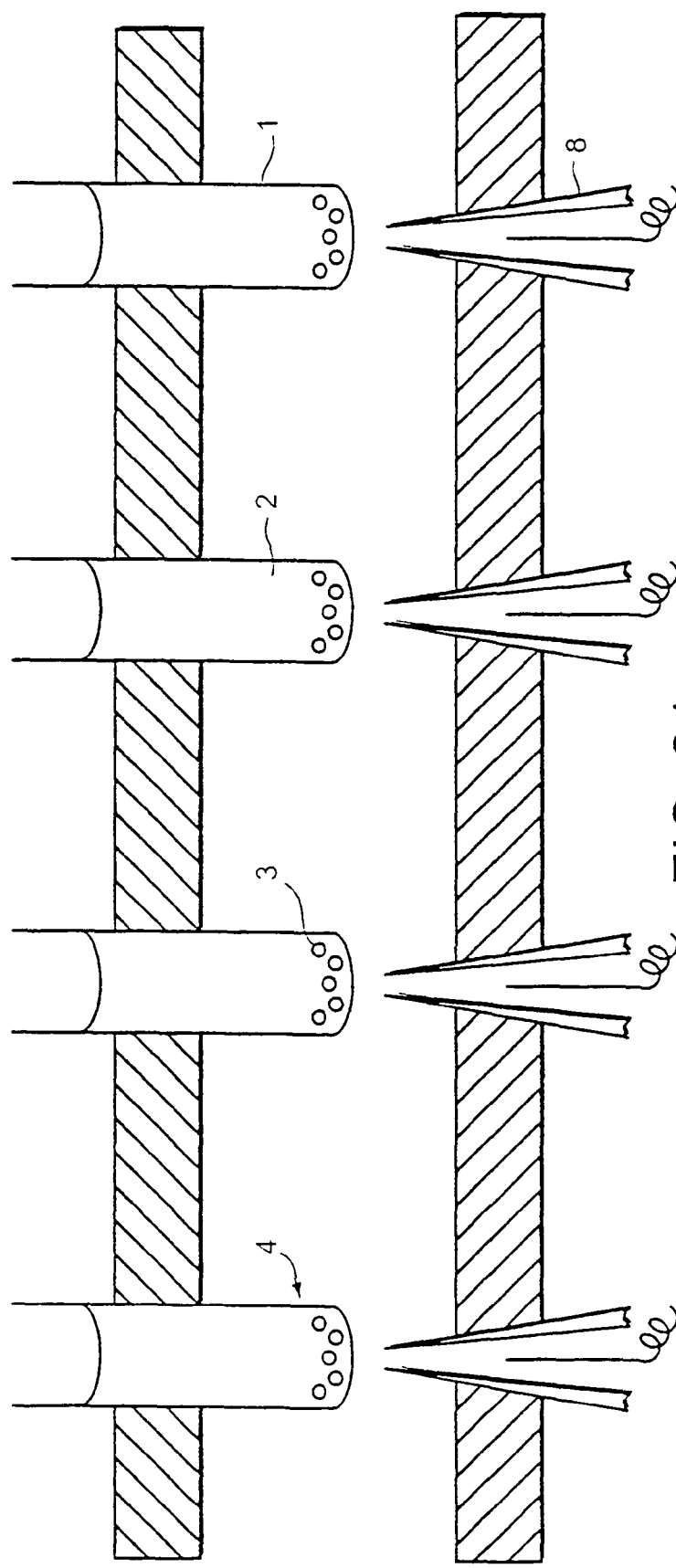
FIG. 24 shows a multiplexed interface patch clamping array.

As has already been mentioned, the arrangement shown in FIG. 23 as well as the arrangement shown in FIG. 24 allows for the formation of a matrix of cell suspensions so that multiple electrodes can be multiplexed to take readings either simultaneously or sequentially (as well as singly).

Figure 25:
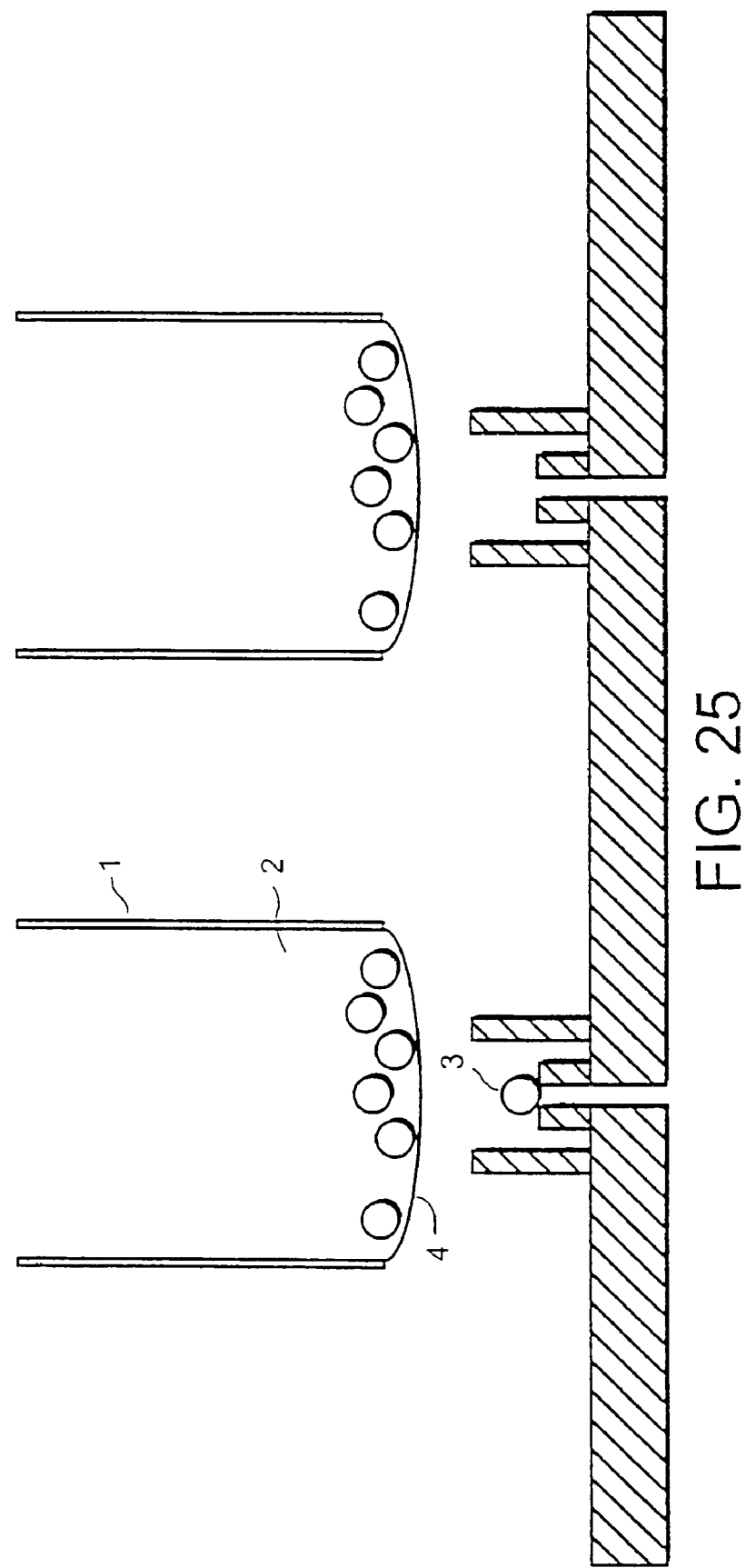
FIG. 25 shows an alternative form of electrode microstructure according to the invention.

It will be appreciated by those skilled in the art that a conventional glass "patch pipette" could be replaced by an equivalent electrode. It is considered to be within the scope of the present invention that the electrode might be either a single region or a matrix of regions on a sheet of material (such as a silicon wafer) which incorporates a microstructure to which a cell can be attached and which would provide the necessary electrical connection. For example, as shown in FIG. 25, microstructures could be etched on to a silicone wafer (e.g. an oxidized silicon wafer), which microstructures would be designed and adapted to be able capture a cell from the liquid/air interface of an arrangement according to the present invention. Thus, the performance and advantage of the invention is not limited to the currently preferred conventional glass patch pipette but would include functionally equivalent means.

As has been described before, a drug in liquid solution can be applied to the cell in a number of ways. For example the drug could be applied via the capillary if the air interface is formed in a capillary tube. Alternatively the drug can be applied by perfusion into a dish (as described with reference to FIGS. 4 to 7). Furthermore, perfusion could be achieved by flowing the drug-containing liquid through a dish or container as shown in FIG. 22.

Figure 26B:
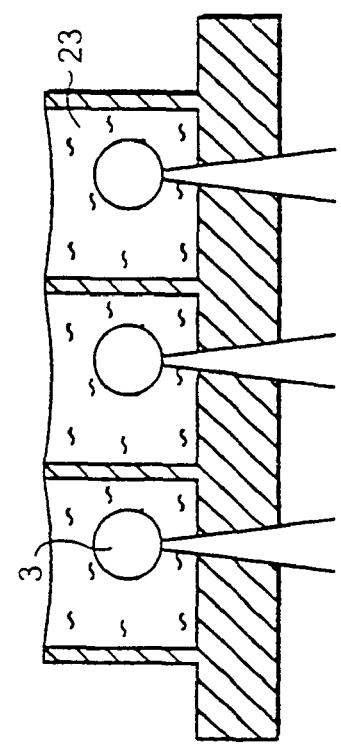
FIGS. 26a and b show a multiwell arrangement for drug application to patch-clamped cells.
Figure 26A:
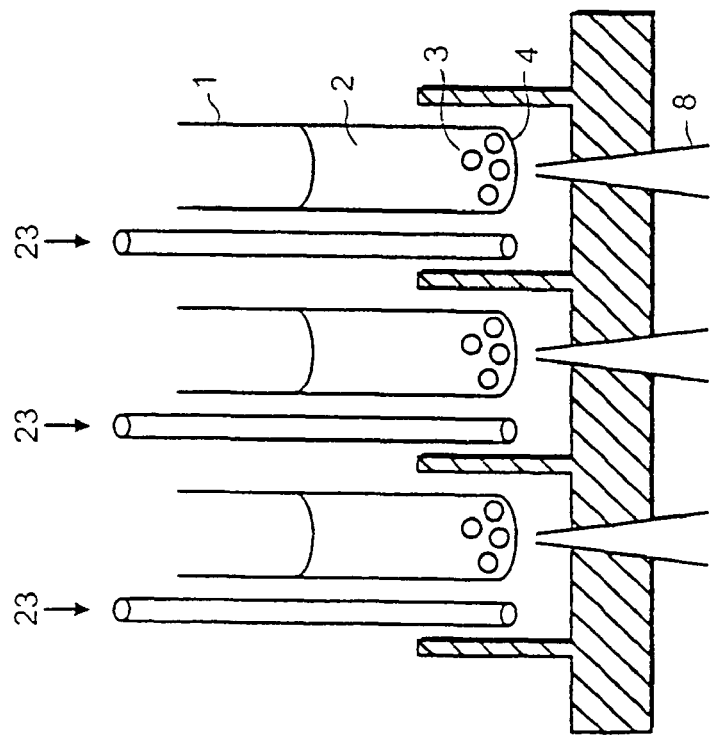

A further arrangement for drug application is shown in FIGS. 26a and 26b. In this case the electrode (for example the patch pipette) penetrates through the lower wall of a well. A suspension of cells is loaded in to a capillary tube as previously described. Attachment of a single cell to each pipette tip follows, as described before. Once cells are attached to the pipette tips the capillary tubes containing the remainder of the cells in suspension can be removed. Subsequently, a drug solution (23) is dispensed into each well (FIG. 26b) and patch clamp measurements can then be carried out on the cell in the environment of the surrounding drug solution.

Optimization of Patch Clamping Conditions

Those skilled in the art will appreciate that within the general teaching contained herein for the interface patch clamping method and apparatus, it may be necessary to optimize certain conditions for patch clamp measurements. For example the concentration and packing density of cells in the suspension may need to be optimized. Furthermore, the cells and/or solutions may be temperature sensitive and an optimum temperature of operation may need to be determined. Since the invention relies on the formation of a liquid/air interface at which the cells are located, it may be necessary to optimize the osmolarity of the suspending liquid medium in order to achieve the optimum level of surface tension etc.

The invention claimed is:

1. A method for providing a cell attached to a patch clamp electrode having a high resistance electrical seal between an area of the cell membrane and the electrode, comprising:
   i) providing a suspension of cells in a liquid such that a layer of cells forms at an interface between the air and said liquid; and
   ii) bringing a patch clamp electrode into contact with the cell membrane of at least one cell by moving one or both of the electrode and the interface respectively together such that a high resistance electrical seal forms between said patch clamp electrode and said cell membrane thereby attaching said at least one cell to said patch clamp electrode.

2. A method for providing a cell attached to a tip of a patch clamp pipette and having a high resistance electrical seal between an area of the cell membrane and the tip, comprising:
   i) providing a capillary tube containing a suspension of cells in a liquid such that a layer of cells forms at one end of the capillary tube at an interface between the air and liquid in which the cells are suspended;
   ii) bringing the top of the patch clamp pipette into contact with the cell membrane of at least one cell by moving one or both of the pipette and the tube respectively together along a common axis of movement such that a high resistance electrical seal forms between said patch clamp pipette tip and said cell membrane thereby attaching to at least one said cell to said patch clamp pipette.

3. The method according to claim 1, or 2, wherein the liquid in which the cells are suspended is an extracellular physiological solution.

4. The method according to claim 1 or 2 wherein the layer of cells is several cells deep and loosely packed.

5. The method according to claim 2 wherein the layer of cells is formed by mounting the capillary tube in an essentially upright orientation and allowing the suspended cells to sediment to the downward end of the tube to collect substantially in a layer.

6. The method according to claim 2 wherein the capillary tube is mounted essentially upright with the interface at a lower open end of the capillary tube and the pipette is mounted essentially upright with the tip upwardly pointing.

7. The method according to claim 2 wherein the capillary tube and pipette are concentrically mounted with the capillary tube in a fixed position and the pipette movable along the common axis.

8. The method according to claim 2 wherein the capillary tube and pipette are concentrically mounted with the pipette in a fixed position and the capillary tube movable along the common axis.

9. The method according to claim 2 wherein suction is applied to the pipette during contact with the interface and during the step of contacting the tip with a cell.

10. A method according to claim 2, in which contact between the pipette tip and the air/liquid interface and/or subsequent movement of the pipette tip into the liquid is detected by monitoring pipette capacitance.

11. A method for providing a cell attached to a patch clamp electrode, comprising:
    providing a suspension of cells in a liquid such that a layer of cells forms at an interface between the gaseous environment and said liquid; and
    bringing a patch clamp electrode into contact with the cell membrane of at least one cell by moving one or both of the electrode and cell membrane together along the common axis such that a high resistance electrical seal forms between said patch clamp pipette tip and said cell membrane thereby attaching to at least one said cell to said patch clamp pipette.

12. The method of claim 11 wherein said interface is formed in a capillary tube.

13. The method of claim 11, wherein said high resistance electrical seal provides a resistance of at least 1 GOhm.

14. The method of claim 1, wherein said high resistance electrical seal provides a resistance of at least 1 GOhm.

15. The method of claim 2, wherein said high resistance electrical seal provides a resistance of at least 1 GOhm.

* * * * *